(12) United States Patent
Morrison

(10) Patent No.: US 8,940,529 B2
(45) Date of Patent: *Jan. 27, 2015

(54) COMPOSTING APPARATUS

(75) Inventor: Michael Morrison, Launching Place (AU)

(73) Assignee: Global Environment Management (FZC) (AE)

( * ) Notice: Subject to any disclaimer, the term of this patent is extended or adjusted under 35 U.S.C. 154(b) by 402 days.

This patent is subject to a terminal disclaimer.

(21) Appl. No.: 13/161,889

(22) Filed: Jun. 16, 2011

(65) Prior Publication Data

US 2011/0244560 A1 Oct. 6, 2011

Related U.S. Application Data

(62) Division of application No. 11/664,837, filed as application No. PCT/AU2005/001501 on Sep. 30, 2005, now Pat. No. 7,989,200.

(30) Foreign Application Priority Data

Oct. 7, 2004 (AU) ................................ 2004905815
Jan. 27, 2005 (AU) ................................ 2005900340
Apr. 13, 2005 (AU) ................................ 2005901851

(51) Int. Cl.
*C05F 17/02* (2006.01)
*C12M 1/04* (2006.01)
(Continued)

(52) U.S. Cl.
CPC ........ *C05F 17/0205* (2013.01); *G05F 17/0223* (2013.01); *C05F 17/0258* (2013.01); *C12M 21/04* (2013.01); *B09B 3/00* (2013.01)
USPC ..................... 435/290.1; 435/290.4

(58) Field of Classification Search
CPC .. C05F 17/0205; C05F 17/0258; C05F 17/02; C05F 17/0063; C05F 17/0223; C05F 17/0072; C05F 17/0027; C05F 17/0235; C05F 17/0247; C05F 17/0229; C12M 21/04; B09B 3/00
USPC ........ 435/290.1–290.4; 34/84, 109, 541, 585, 34/588; 71/23, 24; 210/601, 612, 613, 630
See application file for complete search history.

(56) References Cited

U.S. PATENT DOCUMENTS 4,352,888 A 10/1982 Tisbo et al.
5,190,572 A * 3/1993 Long ................................ 71/9

(Continued)

FOREIGN PATENT DOCUMENTS

AU 199963135 B2 6/2000
DE 39 03 947 A1 8/1990
(Continued)

OTHER PUBLICATIONS

Fernwarme-Tech; "Air Supply Conduits Below Compost Forming Floor"; Derwent Abstract Accession No. 1990-254850/34 of DE 3903947, Aug. 16, 1990.
(Continued)

*Primary Examiner* — Michael Hobbs
(74) *Attorney, Agent, or Firm* — Finnegan, Henderson, Farabow, Garrett & Dunner LLP

(57) ABSTRACT

A composting apparatus comprising a container for receiving material to be composted a base member in the apparatus for supporting material to be composted and the compost when formed, the base having a curved lower wall and an upper opening to define a volume for receiving a drainage medium, a leachate chamber formed in the wall so that when leachate forms, the leachate is able to flow through the medium into the chamber; and an outlet from the chamber for supplying the leachate to the outside of the container.

12 Claims, 21 Drawing Sheets

(51) Int. Cl.
  *C12M 1/107* (2006.01)
  *B09B 3/00* (2006.01)

(56) References Cited

U.S. PATENT DOCUMENTS

| 5,490,604 | A | | 2/1996 | Alexander |
| 5,843,768 | A | * | 12/1998 | Lin et al. ............... 435/290.1 |
| 2002/0081717 | A1 | | 6/2002 | Morrison |

FOREIGN PATENT DOCUMENTS

| DE | 42 05 677 A1 | 8/1993 |
| DE | 44 32 048 A1 | 3/1996 |
| DE | 196 07 789 C1 | 9/1997 |
| JP | 7-277866 | 10/1995 |
| WO | WO-94/29241 | 12/1994 |
| WO | WO-97/19901 | 6/1997 |
| WO | WO-01/40140 A1 | 6/2001 |

OTHER PUBLICATIONS

Wolf; "Compost and Rubbish Aeration Column"; Derwent Abstract Accession No. 1993-273905/35 of DE 4205677 A1, Aug. 26, 1993.
Hauraton GmbH & CO KG; "Composting Plant Designed for Well Distributed Aeration, Avoiding Blockage"; Derwent Abstract Accession No. 1997-426482/40 of DE 19607789 C1, Sep. 11, 1997.
International Search Report mailed Dec. 19, 2005 in PCT/AU2005/001501.

* cited by examiner

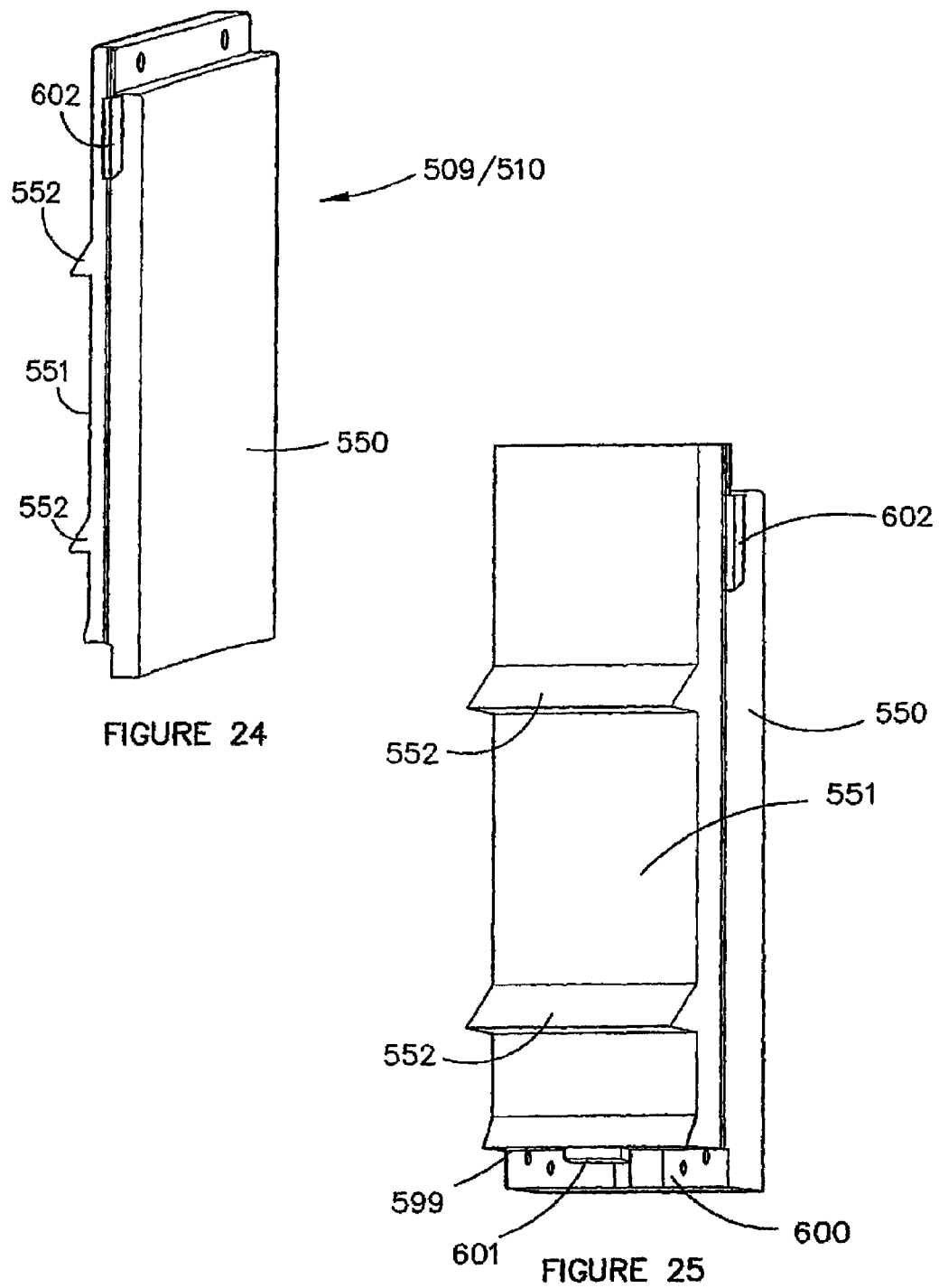

COMPOSTING APPARATUS

This is a divisional application of U.S. patent application Ser. No. 11/664,837 now U.S. Pat. No. 7,989,200 B2, filed on 2 Oct. 2007 that has been incorporated herein by reference.

FIELD OF THE INVENTION

This invention relates to a composting apparatus or composting material.

BACKGROUND OF THE INVENTION

Composting is an environmentally friendly way of disposing of waste organic material. Generally in order to provide good compost, it is desirable that the material aerobically decompose. By providing the right environment for aerobic decomposition, the material can quickly decompose and the quality of the compost is improved.

It is also desirable to collect leachate which drains from the composting material for separate use or to dispose of rather than to allow the leachate simply to drain to the ground.

Composting containers may be required in various different sizes to suit particular applications.

SUMMARY OF THE INVENTION

An object of the first invention is to provide a composting apparatus which improves aerobic decomposition of the material to produce good compost.

The invention may therefore be said to reside in a composting apparatus, comprising:
  a container for receiving material to be composted;
  an aerator in the container, the aerator having at least one opening for allowing air to pass from the aerator into the container for facilitating aerobic decomposition of the material to form compost;
  an air flow path for providing air from outside the apparatus to the aerator; and
  an anti-compaction member for preventing the compost when formed from compacting down on the aerator to allow air flow from the aerator through the at least one opening to the inside of the container.

Thus, the anti-compaction member prevents the compost material from compacting down around the aerator which could block the at least one opening and prevent air from entering the interior. Therefore, good air flow does take place from the aerator to the container to provide the right conditions for aerobic decomposition of the material as material is added to the container and compost builds up about the aerator.

In one embodiment the aerator comprises an upstanding pipe having the at least one opening.

In one embodiment the anti-compaction member comprises a cap located on the pipe and having an outer periphery which is arranged outwardly of the periphery of the pipe.

In one embodiment the anti-compaction member comprises a generally circular disc having a recess so that the pipe can be accommodated in the recess to support the anti-compaction member on the pipe.

In the preferred embodiment of the invention the aerator comprises a substantially conical member having a lower periphery and an upper portion, a peripheral wall tapering inwardly from the lower periphery to the upper portion, and a plurality of vanes on the outer surface of the peripheral wall, the conical member being supported by a pipe in communication with the air flow path so air is able to flow through the pipe to the conical member to the interior of the conical member and escape from the bottom periphery of the conical member, and wherein the anti-compaction member comprises a plurality of vanes on the outer surface of the peripheral wall which prevent composting material from compacting down onto the peripheral wall, and therefore provide a flow passage up the peripheral wall so air is able to flow between the vanes and migrate into the composting material.

Preferably a second pipe is located on the aerator and a second said conical member is located on the second pipe so that air flowing between the vanes of the aerator is able to enter the second pipe and pass to the interior of the second aerator where it exits the second aerator around the bottom periphery of the second aerator to migrate into the material.

Preferably the conical member includes a plurality of flutes at the upper portion for defining a stud onto which the second pipe locates so that air is able to flow from between the vanes of the conical member into the pipe between the flutes and then to the second conical member.

Preferably each of the conical members has a plurality of vanes on an inner surface of the peripheral wall for directing air flow from the respective pipe on which the conical member is located downwardly to the bottom periphery of the respective conical member.

In one embodiment the air flow path comprises a pipe for receiving air from outside the apparatus and conveying the air to the aerator.

In one embodiment the apparatus includes a base member having a lower wall and a chamber formed in the lower wall, the base member being for receiving drainage medium so that leachate from the compost can drain through the drainage medium into the leachate chamber.

In one embodiment a drainage cover is provided on the leachate chamber, the drainage cover having at least one opening for allowing leachate to drain through the cover to the chamber.

In one embodiment the chamber has an outlet pipe for allowing leachate to drain from the chamber to the exterior of the container.

In one embodiment the base includes an upstanding stem and the aerator is supported on the upstanding stem.

In one embodiment the container comprises a plurality of container segments which are connectable one above the other to form the container so that additional segments can be added to increase the size of the container when desired.

In one embodiment each segment has a peripheral wall having an opening so that the opening can receive the pipe for providing air to the aerator or the pipe for draining leachate from the chamber.

In one embodiment the base is supported on an upper edge of a lowermost segment and a second segment of the plurality of segments is arranged on the lowermost segment.

In one embodiment the lowermost segment has a support post for supporting the leachate chamber.

In the preferred embodiment the base includes a base wall having at least one aperture for allowing moisture to drain from the material through the base wall, a leachate chamber connected to the underside of the base wall, the leachate chamber having an outlet for discharge of liquid from the leachate chamber.

Preferably the base wall forms the top of the leachate chamber.

Preferably the leachate chamber includes part of the air flow passage for providing air from outside the apparatus to the aerator.

In one embodiment each segment is formed from three sections to define the peripheral wall. The peripheral wall may be of any desired shape, such as cylindrical, square, rectangular, oval or the like.

In the preferred embodiment of the invention each container segment comprises first and second opposite wall sections each having a central wall portion and two side wall portions arranged at an angle with respect to the central wall portion, and third and fourth opposed flat wall sections which locate between the first and second wall sections.

Preferably a second container segment is arranged on the container segment, the second container segment being substantially the same as the first container segment but rotated 90° with respect to the first container segment.

Preferably the flat wall sections include integral plugs which project inwardly into the composting apparatus for delivering ancillary air to the material.

In still other embodiments the segments may include interlocking connector members for interlocking the segments together.

In another embodiment each segment is formed by a peripheral wall having a first portion and a second portion located inwardly of the first portion so that when the segments are located one above another, the first portion of one segment overlaps the second portion of the adjacent segment to hold the segments together.

In one embodiment the base is provided with a water permeable mat so that microbes can live on the mat and can form a bio-filter for water which passes through the water permeable mat through the base to the leachate chamber.

In one embodiment the container has a tub which receives the base and the leachate chamber and the tub forms a leachate collection tub for the collection of leachate from the chamber and from the container.

In one embodiment the mat is formed from plastic fibre or organic fibre material. The organic fibre material may be coconut palm.

In one embodiment the air inlet is provided above the base to the aerator so that air passing through the inlet is heated by the composting activity within the container to provide warm air to the aerator.

In one embodiment of the invention the container has a peripheral wall having an opening;
  a plug located in the opening, the plug having;
    a front; and
    an air flow director for directing air flow from the front to a location inwardly of the peripheral wall of the container.

In one embodiment the front includes a plurality of openings and the air director comprises a chamber which projects inwardly of the peripheral wall.

In one embodiment the chamber has a first chamber part in which an insulating material is located, and an open second chamber part inclined upwardly from the first chamber part, the inclined chamber part having an upper wall and a lower wall, and at least one opening in the lower wall for allowing air to exit the chamber into the composting device inwardly of the peripheral wall.

In one embodiment the front has at least one drainage opening.

An object of the second aspect of the invention is to provide for the collection of leachate which drains from the composting mass in a composting apparatus.

This aspect of the invention may be said to reside in a composting apparatus, comprising:
  a container for receiving material to be composted;
  a base member in the apparatus for supporting material to be composted and the compost when formed, the base having a curved lower wall and an upper opening to define a volume for receiving a drainage medium, a leachate chamber formed in the wall so that when leachate forms, the leachate is able to flow through the medium into the chamber; and
  an outlet from the chamber for supplying the leachate to the outside of the container.

In one embodiment the lower wall includes a substantially annular curved wall portion, and a downwardly extending wall section which defines the leachate chamber.

In one embodiment the container includes an aerator for supplying air from outside the container to the interior of the container for facilitating aerobic decomposition of material when located in the container to form the compost.

In a still further embodiment of the invention the container includes a lid, the lid having a hole for communicating a cavity in the lid with the container, a layer of insulating material in the lid between the cavity and the container when the lid is located on the container, the lid having an upper wall so that the cavity is located also between the upper wall and the insulating material, whereby water vapour which passes through the opening and into the cavity is condensed on the upper wall so that the water can flow to an outlet collection point from the upper wall.

In one embodiment the base is provided with a water permeable mat so that microbes can live on the mat and can form a bio-filter for water which passes through the water permeable mat through the base to the leachate chamber.

In one embodiment the container has a tub which receives the base and the leachate chamber and the tub forms a leachate collection tub for the collection of leachate from the chamber and from the container.

In one embodiment the mat is formed from plastic fibre or organic fibre material. The organic fibre material may be coconut palm.

In one embodiment the air inlet is provided above the base to the aerator so that air passing through the inlet is heated by the composting activity within the container to provide warm air to the aerator.

In one embodiment the container is formed in a plurality of segments so that a number of segments can be located one above another to form a container of the required size, or to increase the size of the container.

In one embodiment the base is supported on an upper edge of a lowermost of the segments.

In one embodiment the aerator comprises an upstanding pipe having the at least one opening.

In one embodiment the aerator has an anti-compaction member located on the pipe and having an outer periphery which is arranged outwardly of the periphery of the pipe.

In one embodiment the anti-compaction member comprises a generally circular disc having a recess so that the pipe can be accommodated in the recess to support the anti-compaction member on the pipe.

In one embodiment the air flow path comprises a pipe for receiving air from outside the apparatus and conveying the air to the aerator.

In one embodiment a drainage cover is provided on the leachate chamber, the drainage cover having at least one opening for allowing leachate to drain through the cover to the chamber.

In one embodiment the outlet is a pipe for allowing leachate to drain from the chamber to the exterior of the container.

In one embodiment the base includes an upstanding stem and the aerator is supported on the upstanding stem.

In one embodiment the container comprises a plurality of container segments which are connectable one above the other to form the container so that additional segments can be added to increase the size of the container when desired.

In one embodiment each segment has a peripheral wall having an opening so that the opening can receive the pipe for providing air to the aerator or the pipe for draining leachate from the chamber.

In one embodiment the base is supported on an upper edge of a lowermost segment and a second segment of the plurality of segments is arranged on the lowermost segment.

In one embodiment the lowermost segment has a support post for supporting the leachate chamber.

In one embodiment each segment is formed from three sections to form a peripheral wall. The peripheral wall may be of any desired shape, such as cylindrical, square, rectangular, oval or the like.

In still other embodiments the segments may include interlocking connector members for interlocking the segments together.

In another embodiment each section is formed by a peripheral wall having a first portion and a second portion located inwardly of the first portion so that when the segments are located one above another, the first portion of one segment overlaps the second portion of an adjacent segment to hold the segments together.

In one embodiment of the invention the container has a peripheral wall having an opening;
  a plug located in the opening, the plug having;
  a front; and
  an air flow director for directing air flow from the front to a location inwardly of the peripheral wall of the container.

In one embodiment the front includes a plurality of openings and the air director comprises a chamber which projects inwardly of the peripheral wall.

In one embodiment the chamber has a first chamber part in which an insulating material is located, and an open second chamber part inclined upwardly from the first chamber part, the inclined chamber part having an upper wall and a lower wall, and at least one opening in the lower wall for allowing air to exit the chamber into the composting device inwardly of the peripheral wall.

A further aspect of the invention is concerned with the size of the container and enabling the container to be increased in size if desired.

This aspect of the invention may be said to reside in a composting apparatus, comprising:
  a container for receiving material to be composted;
  the container being formed from a plurality of separate segments, each segment including an outer peripheral wall; and
  wherein the segments are located one above another in order to form the composting container and the size of the composting container can be increased by adding additional segments to an uppermost one of the segments.

Thus, by providing the container in the form of a number of segments, a composting container of a particular size can be selected by stacking, for example, one segment above another As composting material builds up or it is otherwise desired to increase the size of the container, an additional segment can be added to the uppermost segment, and so on, to increase the size of the apparatus.

Preferably an aerator is provided for supplying air from outside the container for facilitating aerobic decomposition of the material in the container.

Preferably the aerator can be increased in size as the number of segments is increased by locating a further aerator on the said aerator so that air is supplied to new material added to the container to facilitate the aerobic decomposition of that material.

In the preferred embodiment of the invention each container segment comprises first and second opposite wall sections each having a central wall portion and two side wall portions arranged at an angle with respect to the central wall portion, and third and fourth opposed flat wall sections which locate between the first and second wall sections.

Preferably a second container segment is arranged on a first container segment, the second container segment being substantially the same as the first container segment but rotated 90° with respect to the first container segment.

Preferably the flat wall sections include integral plugs which project inwardly into the composting apparatus for delivering ancillary air to the material.

Preferably each wall section of the container segment has a lower shoulder and a downwardly projecting flange with a peripheral ledge and an upstanding flange respectively of the base.

Preferably each wall section comprises an upper ledge and upwardly standing flange for receiving the second container segment.

Preferably the wall sections of the second container segment have a shoulder and downwardly projecting flange and a shoulder for sitting on the ledge and upwardly projecting flange of the wall sections first container wall section.

Preferably the wall sections have cut-outs and lugs for registry together to locate wall sections of the first container segment on the base and wall sections of the second container base on the first container segment.

Preferably each wall section is formed from an outer skin, an inner skin and an insulating block located between the inner skin and the outer skin.

In a still further embodiment of the invention the container includes a lid, the lid having a hole for communicating a cavity in the lid with the container, a layer of insulating material in the lid between the cavity and the container when the lid is located on the container, the lid having an upper wall so that the cavity is located also between the upper wall and the insulating material, whereby water vapour which passes through the opening and into the cavity is condensed on the upper wall so that the water can flow to an outlet collection point from the upper wall.

In one embodiment the base is provided with a water permeable mat so that microbes can live on the mat and can form a bio-filter for water which passes through the water permeable mat through the base to the leachate chamber.

In one embodiment the container has a tub which receives the base and the leachate chamber and the tub forms a leachate collection tub for the collection of leachate from the chamber and from the container.

In one embodiment the mat is formed from plastic fibre or organic fibre material. The organic fibre material may be coconut palm.

In one embodiment the air inlet is provided above the base to the aerator so that air passing through the inlet is heated by the composting activity within the container to provide warm air to the aerator.

In one embodiment each segment is formed from three sections to define a peripheral wall.

In another embodiment, the peripheral wall of each segment comprises a first wall portion and a second wall portion spaced inwardly from the first wall portion so that when the segments are stacked one above the other, the first wall portion of one segment overlaps the second wall portion of an adjacent segment to join the segments together.

Preferably the first and second wall portions are joined by a transition wall portion.

This embodiment may also include an inner wall section for use with the bottom segment for location inwardly of the first wall portion of the bottom segment, and a top wall section for use with the top segment to extend about the second wall portion of the top segment.

An insulating material may be provided in the space between the first wall section of one segment and the second wall section of the adjacent segment.

In one embodiment the aerator comprises an upstanding pipe having the at least one opening.

In one embodiment an anti-compaction member is located on the pipe and has an outer periphery which is arranged outwardly of the periphery of the pipe.

Preferably the anti-compaction member comprises a generally circular disc having a recess so that the pipe can be accommodated in the recess to support the anti-compaction member on the pipe.

Preferably the apparatus has a pipe for receiving air from outside the apparatus and conveying the air to the aerator.

Preferably the apparatus includes a base member having a lower wall and a leachate chamber formed in the lower wall, the base member being for receiving drainage medium so that leachate from the compost can drain through the drainage medium into the leachate chamber.

Preferably a drainage cover is provided on the leachate chamber, the drainage cover having at least one opening for allowing leachate to drain through the cover to the chamber.

Preferably the chamber has an outlet pipe for allowing leachate to drain from the chamber to the exterior of the container.

Preferably the base includes an upstanding stem and the aerator is supported on the upstanding stem.

In one embodiment of the invention the container has a peripheral wall having an opening;
   a plug located in the opening, the plug having;
   a front; and
   an air flow director for directing air flow from the front to a location inwardly of the peripheral wall of the container.

Preferably the front includes a plurality of openings and the air director comprises a chamber which projects inwardly of the peripheral wall.

Preferably the chamber has a first chamber part in which an insulating material is located, and an open second chamber part inclined upwardly from the first chamber part, the inclined chamber part having an upper wall and a lower wall, and at least one opening in the lower wall for allowing air to exit the chamber into the composting device inwardly of the peripheral wall.

The invention may also be said to reside in a base member for a composting apparatus, comprising:
   a curved lower wall and an upper opening to define a volume for receiving a drainage medium;
   a leachate chamber formed in the wall so that when leachate forms during composting, the leachate is able to flow through the medium and into the chamber; and
   an outlet from the chamber for supplying the leachate from the base.

Preferably the lower wall includes a substantially annular curved wall portion, and a downwardly extending wall section which defines the leachate chamber.

The invention may also be said to reside in a lid for a composting apparatus which has a composting chamber in which composting material can compost, and an open portion, the lid comprising:
   a lid member for closing the open portion, the lid member having an upper surface and a lower surface, an opening in the lower surface;
   insulating material located adjacent the lower surface;
   a cavity formed between the insulating material and the upper surface so that when water vapour enters the opening into the cavity, the water vapour can condense against the upper surface and be collected from the upper surface.

The invention also provides a composting apparatus comprising:
   a container for receiving material to be composted, the container having a peripheral wall which defines a composting chamber;
   an opening in the peripheral wall;
   a plug located in the opening, the plug having;
   (i) a front having at least one hole for allowing air to enter the plug from outside the peripheral wall; and
   (ii) an air director for directing the air into the composting chamber inwardly of the peripheral wall so that the air director allows air to enter the device away from the surface of the peripheral wall so the air passes up through the material.

In one embodiment the air director comprises a first chamber portion and a second chamber portion, the first chamber portion being for receiving an insulating material and the second chamber portion being in communication with the first chamber portion and being defined by an upper wall and an upwardly lower wall which taper towards one another, an outlet opening in the lower wall, the outlet opening being arranged above the opening in the front when the device is supported horizontally on the ground.

In a still further embodiment the first chamber portion and second chamber portion are separated by a baffle which has a lower edge arranged below the outlet opening in the lower wall.

In one embodiment the upper wall and lower wall are inclined. However, if the baffle is used, the upper wall can be substantially horizontal.

In the preferred embodiment of the invention the plug is formed integral with a wall section forming part of the peripheral wall and the opening comprises an opening into which the wall section locates so that when the wall section is located in the opening the plug extends inwardly of the inner surface of the peripheral wall.

Preferably the air director comprises a substantially triangular shaped chamber having an upper substantially horizontal wall, an inclined lower wall inclined upwardly from the peripheral wall, and a surrounding peripheral wall, the peripheral wall have a front between the horizontal wall and the inclined lower wall, and a plurality of holes in the front.

Preferably the upper wall has an eave which extends outwardly beyond the front to provide a cover for the holes to prevent material blocking the holes.

Preferably the plug includes a lower outlet opening for allowing discharge of heavy gases formed during composting of the material from the composting apparatus.

In another embodiment of the invention, the air director comprises a tube which passes through the plug, the hole in the front being comprised by an open end of the tube, and the tube having a portion which extends into the composting chamber inwardly of the periphery with a hole adjacent an inner end of the tube in a lower portion of the tube, the tube being inclined so that the open end of the tube is lower than the hole adjacent the inner end of the tube.

Preferably in this embodiment a second tube is provided below the inclined tube, the second tube being arranged horizontally.

Preferably the shoulder is formed on spaced apart vanes located on the inner surface of the peripheral wall.

Preferably the upper portion of the conical member is provided with a plurality of flutes so that a second pipe can be located on the flutes and air which flows up the outer surface of the peripheral wall between the vanes is able to enter the second pipe between the flutes.

Preferably the second pipe locates over the flutes and rests on a shoulder formed on the vanes.

Preferably the flutes are an extension of the vanes and the transition to the flutes forms the shoulder on which the second pipe rests.

Preferably a second said conical member locates on the second pipe to provide a second aerator.

BRIEF DESCRIPTION OF THE DRAWINGS

Preferred embodiments of the invention will be described, by way of example, with reference to the accompanying drawings, in which:

FIG. 24 is a perspective view of a slide wall section;

FIG. 25 is an internal perspective view of the side wall section in FIG. 24;

DETAILED DESCRIPTION OF THE PREFERRED EMBODIMENTS

Figure 1:
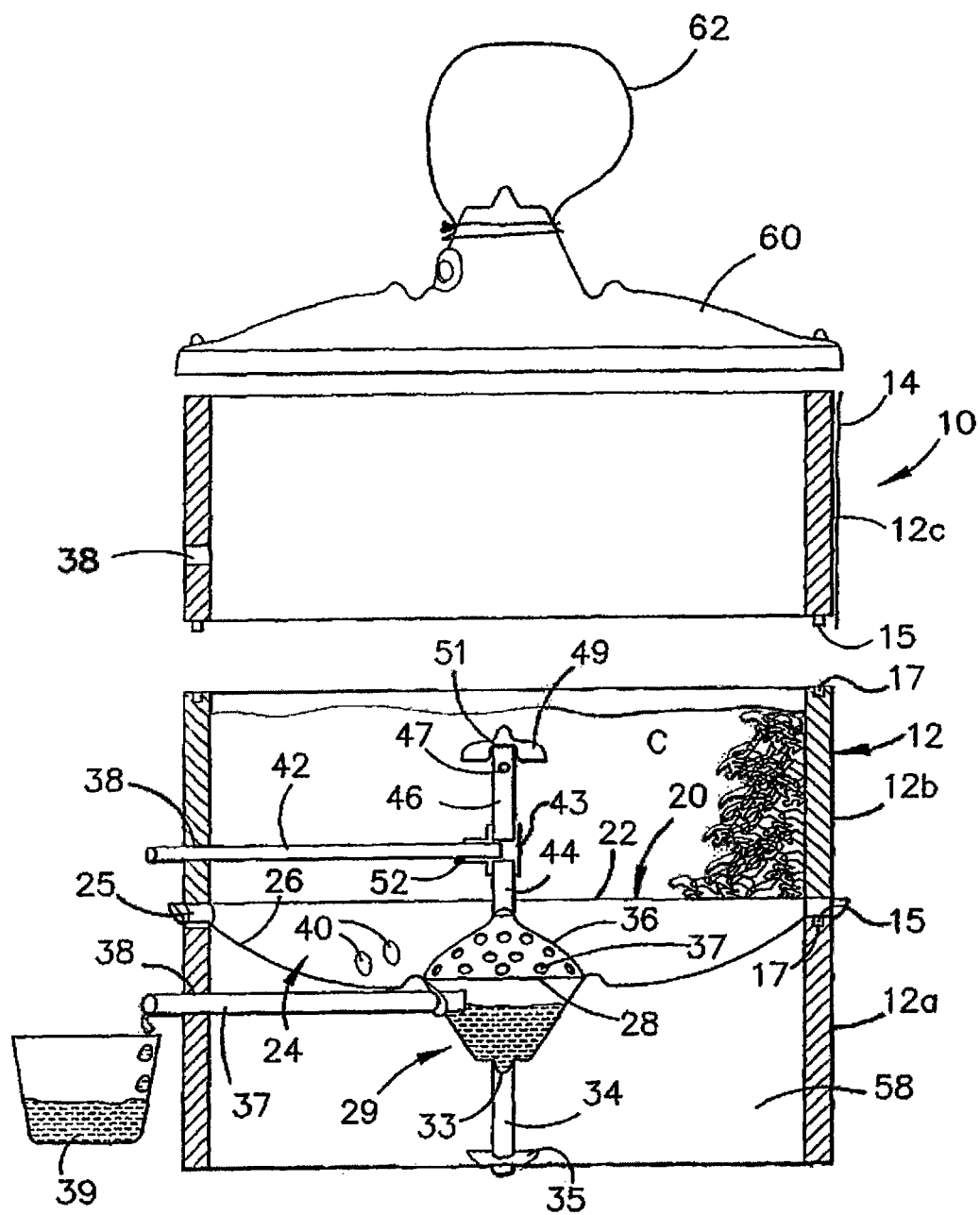
FIG. 1 is a view of a composting apparatus according to one embodiment of the invention.

With reference to FIG. 1, a compost apparatus 10 is shown which has a container 12 formed from a plurality of segments 12a, 12b and 12c. As will be apparent hereinafter, the number of segments which may be used is arbitrary and segments can be added to increase the size of the container as desired. However, in general, at least two of the segments will be used to form a composting apparatus, as will also be described in detail hereinafter.

The segments are generally cylindrical in configuration and define a peripheral wall. The segments are stacked one above the other in order to form the container and a sheath 14 may be slid over the assembled segments to hold the segments together. Alternatively, the segments may include interlocking components such as a small projection 15 at the bottom of the wall of each segment which registers in a correspondingly shaped recess 17 in the top of each wall of the segment.

A base 20 is located in the container 10 and is supported on the lowermost segment 12a. If the interlocking components 15 and 17 are used, the base 20 may have openings through which the projections 15 can project to locate in their respective recesses 17. The base 20 has an upper opening 22 and a peripheral lower wall 24. The peripheral lower wall 24 has an upper wall section 25 which receives the segment 12b and a downwardly curved annular bowl wall section 26. The annular bowl wall section 26 defines an opening 28 and a leachate chamber 29 is located in the wall 24 beneath the opening 28. The leachate chamber 29 has a conical wall 30 which is a continuation of the curved bowl wall 26 and the leachate chamber 29 is completed by a lower bottom wall 31. The lower bottom wall 31 may have a downwardly projected portion 33 which sits in a recess of a post 34 to assist in supporting the leachate chamber 29 and the base 20.

The bottom of the post 34 may have a cup 35 to facilitate support of the posts 34 in contact with the ground.

A drainage cover 36 is provided on the leachate chamber 29 and has a plurality of openings 37 so that leachate can drain through the composting mass and into the leachate chamber 29. The leachate chamber 29 has an outlet pipe 37 which passes through an opening 38 in the peripheral wall of the segment 12a so that leachate can be collected outside the container 10 in a vessel 39 for use as a fertilizer, or the like, or for disposal as required.

The base 9 receives drainage medium 40 which may be in the form of pebbles or the like so that when waste material for composting is loaded into the container, the waste material is supported by the base 9 above the medium 40. Thus, leachate which is formed as the material aerobically decomposes is able to drain through the medium 40 through the holes 36 and into the chamber 29.

The segment 12b, as previously described, is the same as the segment 12a. However, in this case, a pipe 42 which passes through the opening 38 in the segment 12b joins with a T-shaped coupling member 43. The member 43 receives a post 44 which rests on the drainage cover 10 to support the pipe 42 and the coupling 43. An aerator 46 is located to the upper part of the coupling 43 for providing air into the container to facilitate aerobic decomposition of the material in the container. The aerator 46 has at least one opening 47 and, most preferably, a plurality of openings. The coupling 43 provides a passage from the pipe 42 to the aerator 46 so that an air flow path is provided from outside the container through the pipe 42 and the coupling 43 to the aerator 46.

The aerator 46 in this embodiment is in the form of a pipe and an anti-compaction cap 49 sits on the aerator 46 to prevent composting material from compacting around the aerator 46 which would prevent air flow out of the openings 47 and therefore the proper aerobic decomposition of the remaining material in the container. The cap 49 may be a generally disc-shaped cap having a recess 51 into which the top of the pipe which forms the aerator 46 is received. Thus, the cap 49 has an outer periphery which is arranged outwardly of the periphery of the aerator 46 and this therefore tends to prevent the compaction of compost as it is formed around the aerator 46, ensuring that air is able to flow from the aerator 46 through the mass in the container to facilitate the proper aerobic decomposition.

The pipe 42 may have an outlet opening 52 which is located on a lower side of the pipe 42. This would generally be in an area of relatively reduced compaction, and therefore air can enter the container from the hole 52 and disperse under the pipe 42 and down through the medium 40 filtering back up through the composting mass (generally labelled C in FIG. 1).

The base 20 effectively seals the area above the base from lower air space 58 in the segment 12a so that all of the air which enters the container does go through the aerator 46. Because the pipe 38 is raised above ground level, it is in a slightly warmer zone and if it were located at the very base of the container and this assists aerobic decomposition during particularly cold weather.

When the container formed from the segments 12a and 12b is almost full, a further segment (such as the segment 12c) can be added by locating that segment on the segment 12b. When this happens, the cap 49 is removed from the aerator 46 and a further coupling 43 is located on the aerator 46 and a new aerator 46 is then arranged in the upper recess of that new coupling 43. The cap 49 is then placed on the new aerator 46. The pipe 38 can be withdrawn from the segment 12b and located through the hole 38 in the segment 12c to register with the coupling 43 or, alternatively, a new pipe can be located, leaving the old pipe 38 in the segment 12b.

Thus, the segment 12c increases the volume of the container 10 and further material can be added into the container 10 for aerobic decomposition. Additional segments and aerators 46 can be added in the same manner if required.

Figure 7:
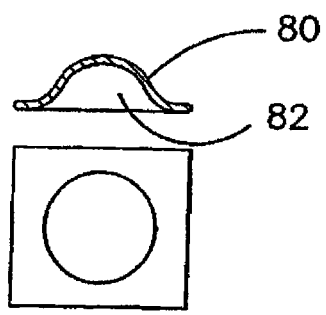
FIG. 7 is a view of a device which may be used with the preferred embodiments.

The uppermost segment of the container is closed by a lid 60 which is preferably insulated and which merely sits over the uppermost segment. The lid 60 may have an outlet opening 61 for allowing gases to be drawn off to both reduce odour and allow for the possibility of burning off of the gas. A bag 62 may be provided for collecting the gas if desired. The aerator pipes 46 and the caps 49 may be formed from decomposable material so they themselves breakdown over time. Furthermore, composting devices 80 shown in FIG. 7 may also be thrown into the composting mass to facilitate composting. The devices 80 help air cavities being formed by defining an air cavity themselves to further facilitate aerobic decomposition. The devices 80 may have fertiliser such as ground eggshell added to them to increase the performance of bacteria.

Furthermore, dry powdered bacterial culture can also be added to help culture specific bacteria which can target specific breakdown of materials in a composting mass, such as meat scraps or other materials which are hard to break down.

Figure 2:
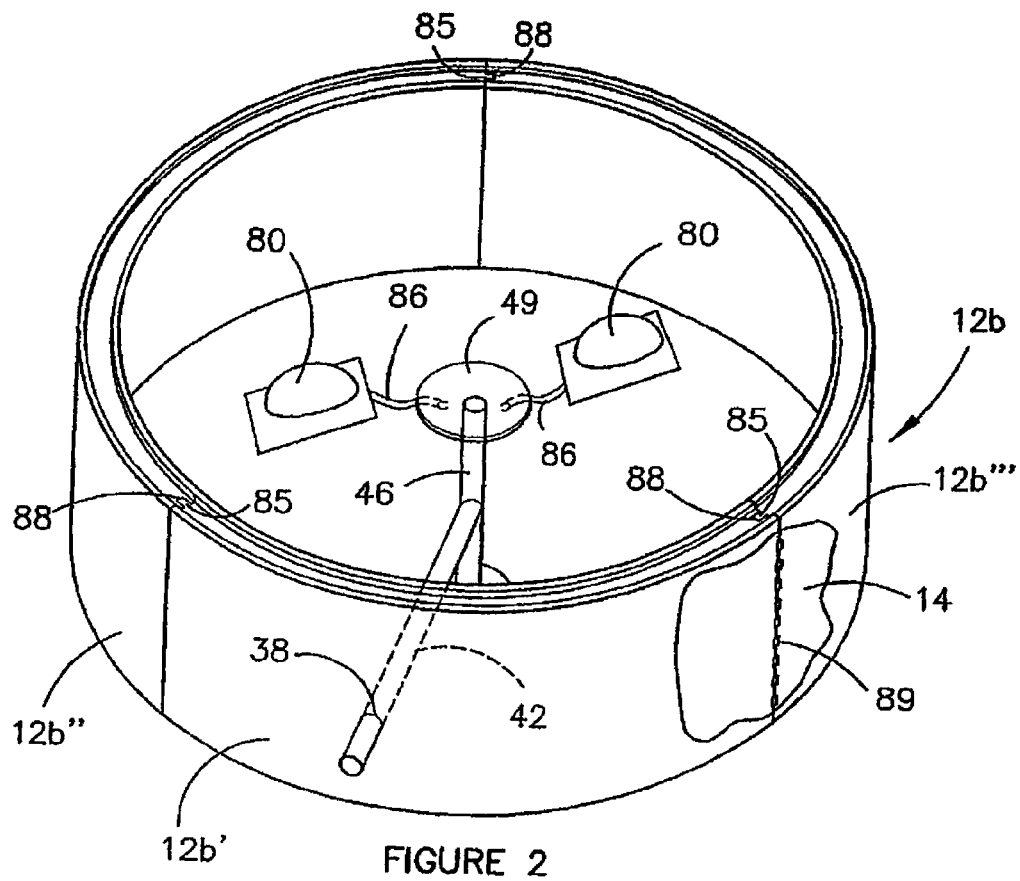
FIG. 2 is a view of one of the segments of the apparatus of FIG. 1.
Figure 3:
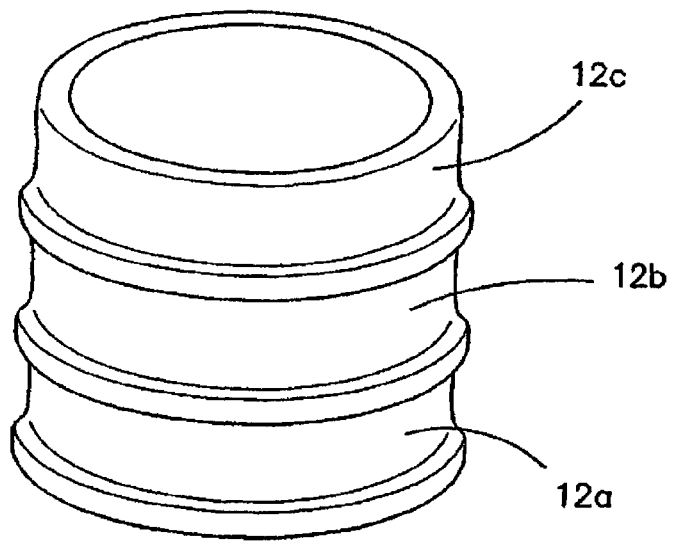
FIG. 3 is a view of a second embodiment of the invention.

As shown in FIG. 2, each of the segments 12a, 12b and 12c (only segment 12b being shown in FIG. 2) may be formed from a plurality of wall sections 12b', 12b'' and 12b'''. The sections may be connected together by interlocking projections 85 on one section which locates in a correspondingly shaped groove 88 in the other section.

FIG. 2 also shows how some of the devices 80 may be arranged with small air tubes 86 to convey air from the aerator 46 to the devices 80.

In one embodiment of the invention, rather than the sheath 14 being in the form of a sleeve which slides over the segments, the sheath may be in the form of a sheet which wraps around the segments and is joined by a fastener 89 such as a Velcro or any other suitable fastener.

Figure 4:
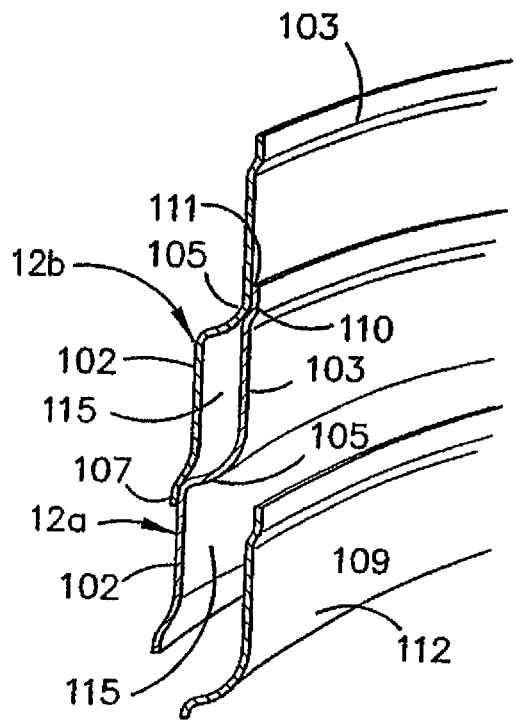
FIG. 4 is a detailed view of part of the embodiment of FIG. 3.

FIGS. 3 to 6 show a second embodiment of the invention. This embodiment is the same as the previous embodiment except that the segments 12a, 12b and 12c are formed in a different way. As shown in FIG. 4, segment 12a is formed from a peripheral wall having a first skin 102 and a second skin 103 which is spaced inwardly of the skin 102. The first skin 102 and the second skin 103 are joined by a slightly inclined transition portion 105.

Thus, the segment 12b is arranged on the segment 12a by locating the first skin 102 of the segment 12b over the second skin of the segment 103 so that the segments effectively clip or lock together. The lowermost part of the skin 102 may be slightly flared out at 107 so that it locks onto the apex 109 formed by the skin 102 and portion 105 and the upper part of the skin 103 may be flared slightly inwardly at 110 so as to receive the apex 111 formed by the portion 105 and skin 103 of the segment 12b.

In this embodiment the segments are complete annular segments rather than being formed in three sections, as in the earlier embodiment.

If desired, a bottom wall segment 112 can be provided. The bottom wall segment 112 is effectively the same as the segments 12a, 12b, 12c from the apex 109 to the flared portion 110. Thus, the segment 112 can sit adjacent the skin 102 of the bottom segment 12a.

When the wall segments are assembled in the manner shown in FIG. 4, cavities 115 are provided between the respective skins and an insulating material in the form of billets of polystyrene 90 may be inserted into the cavities 115.

Figure 5:
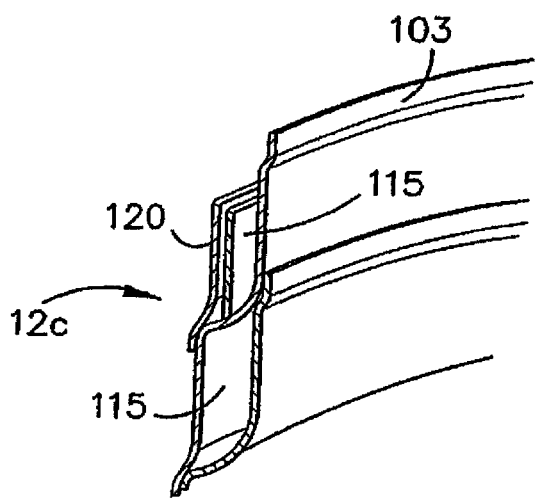
FIG. 5 is a detailed view of part of the embodiment of FIG. 3.
Figure 6:
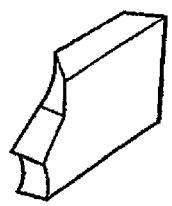
FIG. 6 is a view of a component used in the embodiment of FIG. 3.

As is shown in FIG. 5, the top of the container is completed by a top skin 120 which is generally identical to the part of the segments from the outwardly flared portion 104 up to the apex 111. The skin 102 therefore sits adjacent the second skin 103 of the uppermost segment, i.e. segment 12c, and once again, the polystyrene billets 90 may be located into the cavities 115 which are formed between the respective wall portions.

This embodiment of the present invention has particular advantage in cold climate areas. The reason for this is that the container in both embodiments described can be insulated which assists in maintaining the required heat within the composting apparatus, notwithstanding the cold environment in which the apparatus may be used. Thus, in the embodiment of FIG. 1, the segments may be formed from insulated components and, as previously described in the embodiment of FIGS. 3 and 4, insulating billets can be inserted in between the overlapping components of the segments.

Furthermore, by forming the container from segments, only a few segments can be initially used so that the air space above the composting material initially located in the container is relatively small. Hence, heat which is generated by the composting mass is not lost by simply heating up a relatively large air space above the composting material. As previously explained, as the amount of compost grows and additional material is to be added, the size of the container can be increased by stacking an additional segment. Thus, this maintains the air space above the composting mass relatively small, and heat loss to the air space is minimal.

Furtherstill, rather than simply providing a hole in the lid for escape of gases, a load pressure valve may be provided so that the air cannot escape quickly, therefore also reducing heat loss.

In still further embodiments of the invention, rather than supplying air through the pipe 42 to the aerator, air may be supplied through the leachate drain pipe 37 so that air passes from the outside of the container through the pipe 37 into the chamber 29. The stem 44 may be made hollow so that the air can not only pass up through the medium 40 but also through the hollow stem 44, coupling member 43 and into the aerator 46.

A still further embodiment is described with reference to FIG. 8, in which like reference numerals indicate like parts to those in the embodiment of FIG. 4. As in the embodiment of FIG. 4, the compost container is built up from a number of side wall segments so the height of the container can be changed. The segments comprise a similar configuration to that described with reference to FIG. 4, except that the segments are of a more right-angled configuration at their transition points. Thus, the segments are made up of skin 102 and skin 103 which is arranged inwardly of the skin 102 together with transition section 105. Just above each of the transition section 105 is a ledge or lip 210 which is intended to prevent moisture and water from entering the cavity formed between the skins 102 and 103. As in the earlier embodiment, the lower wall segment 12a is completed by a lower skin 112 which is provided with a ledge 113 which forms the same function as the ledge 210 and an upper skin 120 which forms the same function as the skin 120 in the earlier embodiment.

Figure 8:
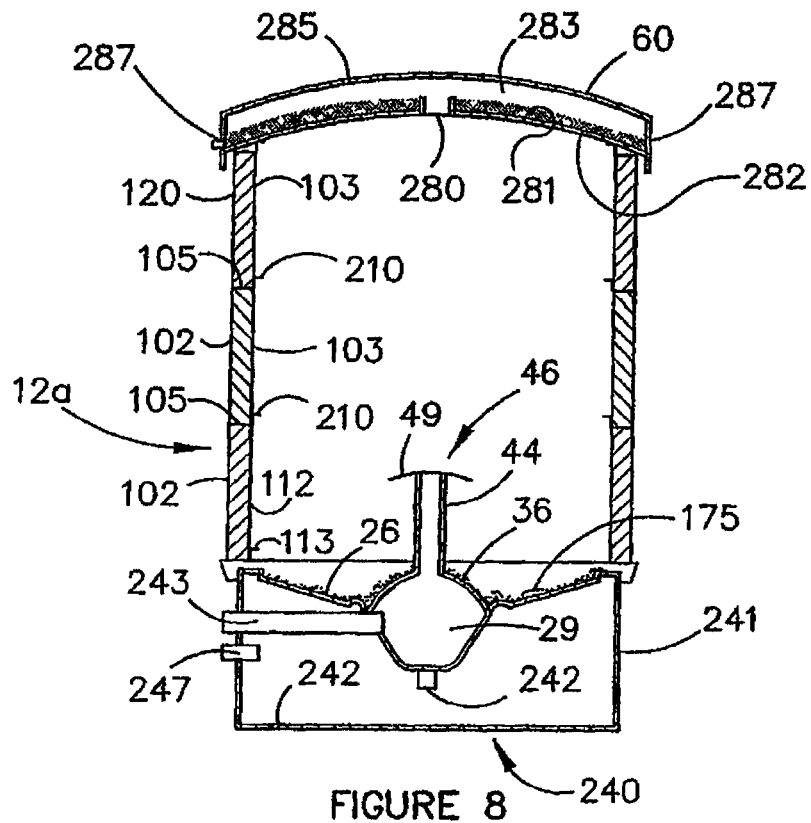
FIG. 8 is a view of a still further embodiment of the invention.

In the embodiment of FIG. 8, rather than the segments 12a, etc. being completely circular, the segments are formed in three parts so that the three parts are located together in the same manner as described with reference to FIG. 1 in order to form the complete circular segment 12a. As in the earlier embodiments, the segments need not be circular, but could be of other shapes, such as square, oval or the like.

In the embodiment of FIG. 8, the base is formed by a tub 240 which has side wall 241 and bottom wall 242. An air inlet pipe 243 is provided through the side wall 241 and communicates with the leachate chamber 29. In this embodiment, the leachate chamber 29 has an open bottom 244 so that the leachate can drain from the chamber 29 into the tub 240. The tub 240 is provided with a small outlet pipe 247 so that leachate can drain from the pipe 247 and be collected.

In this embodiment, the wall 26 may also be provided with openings so that water can drain straight through the wall section 26 into the tub 240.

This embodiment is provided with the same type of aerator as in the earlier embodiments, which are schematically shown by reference numeral 46. Again, the aerator is provided with an anti-compaction cap 49 as in the earlier embodiments.

The wall 26 and drainage cover 36 may be covered by a mat 175 which extends completely over the wall 26 and cover 36. The mat is preferably made from plastic fibre or organic fibre material such as coconut palm, and forms a bio-filter for water draining from the composting material into the tub 240. Microbes are able to live on the mat 175 and as the water drains through the mat, the microbes clean the water which then passes through to the tub 240.

The mat 175 may be of any desired thickness and, if desired, a number of the mats 175 may be provided throughout the compost container as compost builds up in the container.

In a variation of FIG. 8, the air input pipe, rather than communicating with the chamber 29, may communicate with the pipe 44 as in the embodiment of FIG. 1. This arrangement has advantages in cold weather because the warm compost mass within the container will tend to warm the air passing through the pipe 243 which enhances the aerobic decomposition when the air passes through the aerator 46 and into the composting mass.

In still further modifications, the pipe 243 may branch into a plurality of smaller pipes which connect with the pipe 44 so that the effective surface area of the air inlet is increased to thereby increase the heat conduction from the composting material into the air passing into the container.

In this embodiment, lid 60 may simply be an insulated lid, as in the earlier embodiments. Alternatively, the lid 60 may be provided with a central hole 280 and a layer of insulating material 281 on its bottom wall 282. A chamber 283 is formed between the insulating material 281 and upper surface 285 of the lid 60. The insulating material 281 maintains the bottom wall relatively warm and at the same temperature as the internal cavity of the container. Thus, steam rises up through the opening 280, it passes into a cooler region and contact with the upper surface 285, which will be cooler than the interior of the container. Thus, the moisture will condense and will drain along the top surface 285 to outlet holes 287 for collection.

In this embodiment a small groove may be provided in the top surface of the panel section 120 for assisting seating of the lid 60 and also for forming a water channel so that a water seal is formed around the lid to thereby further seal the chamber 283 and the container from the ambient atmosphere.

As in the earlier embodiments, the cavities between the wall panels are filled with insulating material. The ledge 210 which prevents water from entering the cavity may also act as a locating element for locking the wall sections together to improve the sealing of the sections and the strength of the container.

The location of the water outlet pipe 247 above the base 242 of the tub 240 allows sediment to settle in the tub so that cleaner water is produced from the outlet 247. If desired, the run-off water from the outlet pipe 247 can be further filtered to clean the water from pathogens. In still further embodiments not shown, there may be a section within the tub 240 to allow for a clean water storage area and the filter is locatable between that area and the remainder of the tub so that liquid which enters the area is filtered as it passes through the filter from the remainder of the tub.

Finally, the provision of holes in the base plate 26 allows gas to rise so that the compost material in the container acts as a bio-filter to prevent odour from the liquid storage area because of the cleaning affect of the compost material on the rising gas and the cleaning of the gas by the compost in the container.

In alternative embodiments, not shown, no leachate chamber may be provided in the compost apparatus. In this embodiment, the bottom 242 of the tub 240 may simply be omitted so that the peripheral wall 241 simply rests on the ground and leachate drains directly to the ground via chamber 29 which has an open bottom.

The lid of the embodiment of FIG. 8 may be a conventional lid which does not collect condensate. Thus, the hole 280 could be simply omitted and the entire lid formed from an insulating material. In still further embodiments (not shown) the insulating layer 281 may be provided on the bottom surface of wall 282. In a still further embodiment, a layer of insulating material may be provided solely on the bottom surface of upper surface 285, although in such an embodiment, the amount of condensation is likely to be less because the chamber within the lid 60 is likely to be warmer.

Whilst in the preferred embodiments, the invention has been described with peripheral walls formed from three segments, the walls may be formed from two or more segments and each segment may be formed from two or more wall sections to make up each segment.

A still further embodiment of the invention is described with reference to FIGS. 9 to 11. The embodiment of FIGS. 10 to 12 can be used with any one of the configurations previously described but is probably most suitable for the square or rectangular profile of the composting apparatus of FIG. 8. Like reference numerals indicate like parts to those described with reference to FIG. 8.

Figure 9:
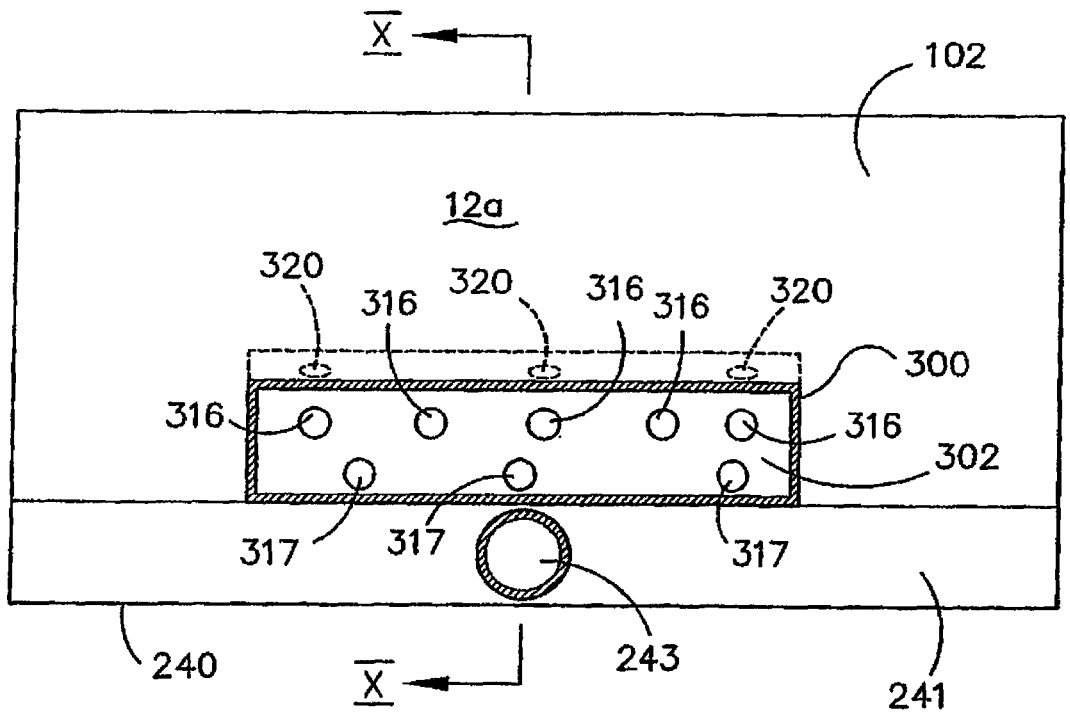
FIG. 9 is a front view of a still further embodiment of the invention.
Figure 10:
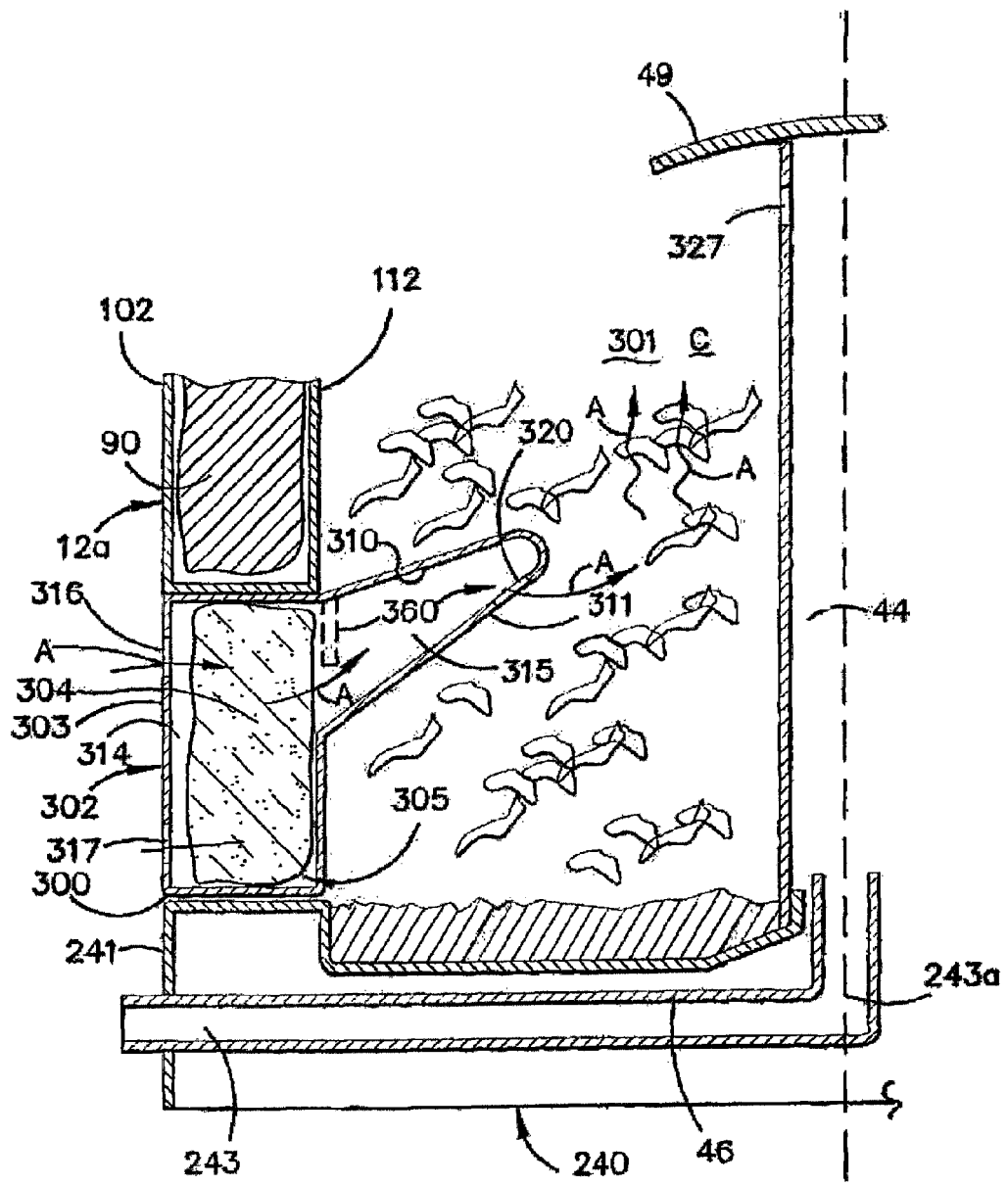
FIG. 10 is a view along the line X to X of FIG. 9.
Figure 11:
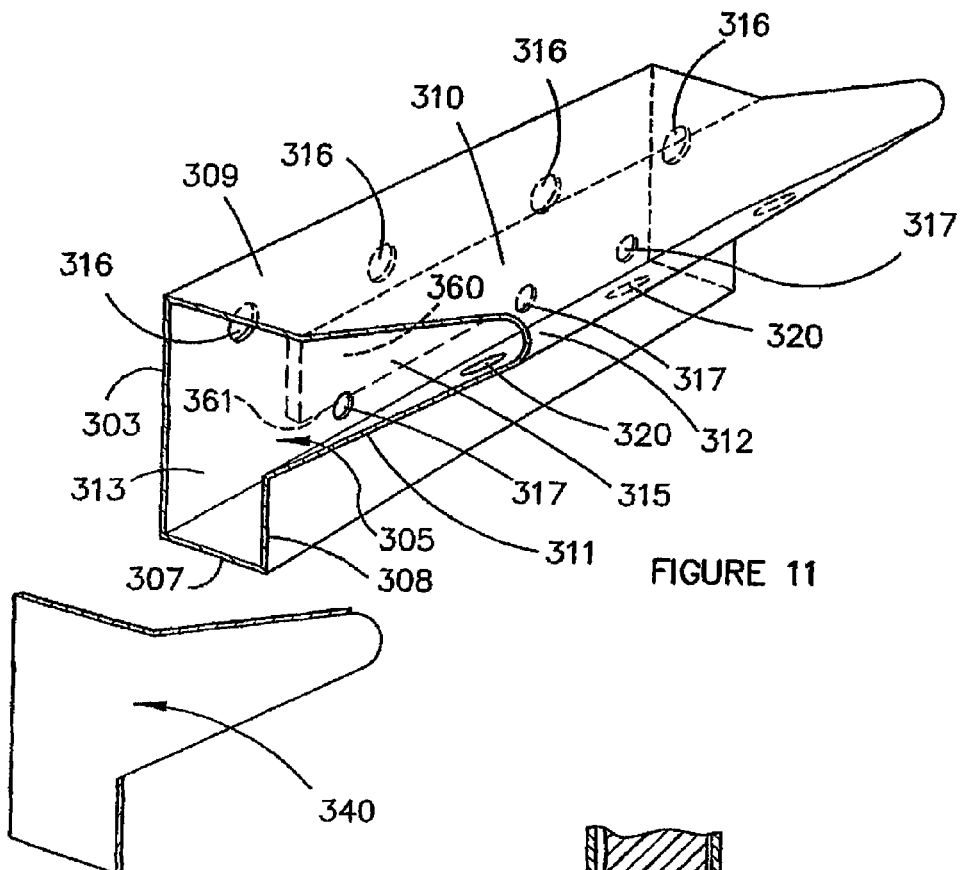
FIG. 11 is a perspective view of part of the embodiment of FIG. 9.

In the embodiment of FIGS. 9 to 11 the lower most segment 12a is provided with a rectangular opening 300. The rectangular opening is closed by a plug 302. An air pipe 243 is located in tub 240 as in the earlier embodiment. However, in this embodiment the pipe 240 has u-shaped turn 243a which joins directly with aerator tube 44 so that there is provided direct to the aerator 44 and not merely into the tub 240 as in the earlier embodiments. Wall 26 of the tub 240 is of a different shape to the earlier embodiment as is also shown in FIG. 11.

As is best shown in FIG. 10 and FIG. 11 the plug 302 has a front 303 which may be integral with the remainder of the plug 302 but which preferably forms a removable front panel 302 so insulating material 304 can be more readily located within the plug 302. The plug 302 has a chamber 305 in which the insulating material 304 is located. The chamber 305 is defined by the front 303, bottom wall 307, inner wall 308, upper wall 309, inclined first wall 310 and inclined second wall 311. The wall 310 and 311 taper towards each other to form a rounded transition 312. The chamber 305 is generally defined by a first chamber portion 313 in which the insulating material 304 locates and a second chamber portion 315 which forms an air directing chamber.

The insulating material 304 also acts as a filter to filer air passing into the chamber 315 from opening 316.

The front 303 has a plurality of holes 316 which provide air inlet openings and at least one lower opening 317 which forms a heavy gas and water outlet opening.

Second inclined wall 311 has a plurality of air outlet openings 320 for allowing air to escape from the plug 302 into the composting mass inwardly of the peripheral wall defined by the skins 102 and 112.

As is apparent from FIG. 11 the holes 320 are slightly above the holes 311 when the device is supported horizontally on the ground.

An air outlet hole 327 may also be provided in aerator 44 slightly below anti-compaction cap 49.

The front 303 may be a clip fit to the remainder of the plug 300 so that after insulating material 304 is located in position the front 303 can be snapped back into position. The end of the plug 302 may be provided with cover plates (one of which is shown at 340 in FIG. 12) for closing the ends.

When the plug 302 is in position air is able to flow through holes 316 into chamber 305. The air flows through the insulating material 340 which is of a porous nature such as an open cell foam and out through holes 320, into composting chamber C generally defined by the segments 12a etc, as shown by arrows A. The provision of the hole 320 in the lower wall 311 prevents the hole 320 from becoming blocked by composting material and the chamber 315 which projects into the composting mass C in compositing chamber 301, inwardly of the peripheral wall defined by the segment 12a locates the air outlet closer to the middle of the composting mass C so the air flows into the composting mass C then up through the composting mass. This prevents the air from simply flowing upwardly in a somewhat "chimney" effect, adjacent the peripheral wall between the side wall and the composting mass C.

The composting mass C which compacts above the wall 310 also facilitates the flow of air up through the middle of the composting mass C rather than along the interior surface of the peripheral wall formed by panel 112 so the air flows through the composting mass C to assist aerobic decomposition.

The fact that the hole 320 is higher than the hole 316 means that gases which are lighter than air will also move up through the composting mass C where the biomass of the compost will clean those gases to some extent helping to reduce odour. Thus, odorous gases are prevented from escaping through the hole 316.

The insulating material 304 in the form of an open cell phone prevents air turbulence inside the plug 300 which further prevents and light gases from escaping through holes 311. The insulating material 304 also prevent insects from entering the composting mass C through the holes 316 and 317.

The holes 317 prevent the build up of carbon dioxide in the bottom of the chamber 301 adjacent wall 46 to a level which could otherwise prevent air from entering the composting mass C through hole 320. The hole 317 also allows water to drain out of the plug 300 should any water condense in the plug 302.

A number of plugs 301 may be provided up the height of the composting apparatus when the apparatus is formed from the plurality of segments 12a-12c as in the earlier embodiments each segment may be provided with a plug 301 so that a number of plugs 301 are located up the container as the size of the container is increased by adding additional segments to the composting apparatus.

The plug 301 may be used with the aerator 44 or instead of the aerator 44. The size of the plug 301 can also be increased in particular the amount the walls 311 and 310 project into the composting mass so as to locate the holes 320 at the desired inward location from the wall panel 112.

The plug 301 is also removable from the composting device as a unit so that the hole 300 can be used as an opening through which composted material is retrieved. The plug 301 may then be reinserted in place for the next load of composting mass to be deposited within the apparatus.

In an alternative embodiment the chamber 305 may be separated from the chamber 315 by a baffle 360 which extends downwardly from upper wall 309. In this embodiment the air movement from the chamber 305 to the chamber 315 is such that the air flows beneath lower edge 361 of the baffle 360. The lower edge 361 is arranged below the level of holes 320. If the baffle 360 is used, the wall 310 may be horizontal and simply a continuation of the wall 309 because the baffle 360 will prevent gases which are lighter than air from flowing from the chamber 315 to atmosphere through the openings 316.

By arranging the upper wall 310 and also possibly the lower wall 311 horizontally rather than inclined, as in FIG. 11, the plug 301 will be easier to remove from the opening 300. In the embodiment shown in FIGS. 10 and 11, a slight rotation of the plug is necessary when removing the plug so that the walls 310 and 311 can move out through the opening. If the walls 310 and 311 are horizontal and the plug can be pulled straight outwardly from the opening 300.

Figure 12:
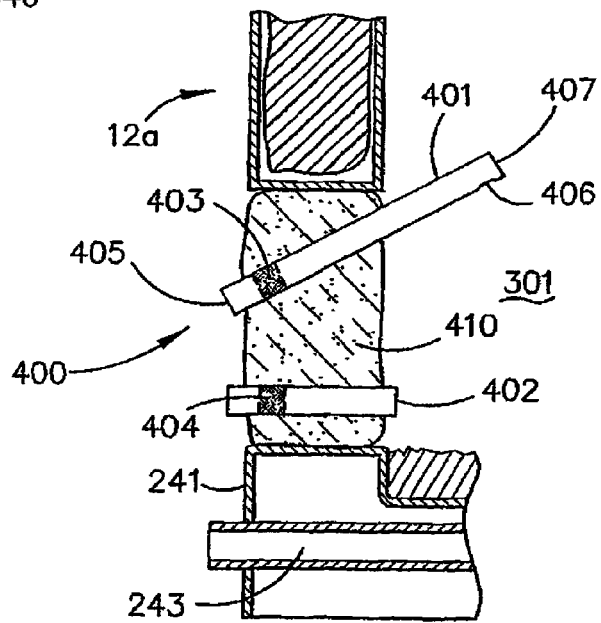
FIG. 12 is a view of a further embodiment of the invention.

FIG. 12 shows a still further embodiment of the invention in which like reference numerals indicate like parts to those previously described. In this embodiment the plug 400 is formed from a block of insulating material 410. The insulating material 410 may have a surrounding cover (not shown) of plastics material if desired. A first inclined tube 401 passes through the block 410 and has an open outer end 405. A hole 406 is located in a lower part of the tube 401 adjacent inner end 407 so that air can enter the end 405, flow through the tube 401, and then exit through the opening 406. By providing the opening 406 in the lower part of the tube 401, the opening 406 will not become blocked by composting material within the chamber 301.

A second tube 402 is arranged below the tube 401 and is generally horizontal. The tube 402 is open at both ends and provides an outlet for carbon dioxide which may accumulate at the bottom of the chamber 301. The tubes 401 and 402 may be provided with a gauze filter 403 and 404 respectively to prevent insects from entering the chamber 301. The plug 400 may generally be the same size as the plug 301 described with reference to FIG. 11. The opening 405 and the opening 406 perform the same functions as the holes 316 and 320 in FIG. 11. If desired, a plurality of tubes 401 can be provided in each plug 400. The open ends of the tube 402 function in the same manner as the openings 317 in FIG. 11.

Figure 13:
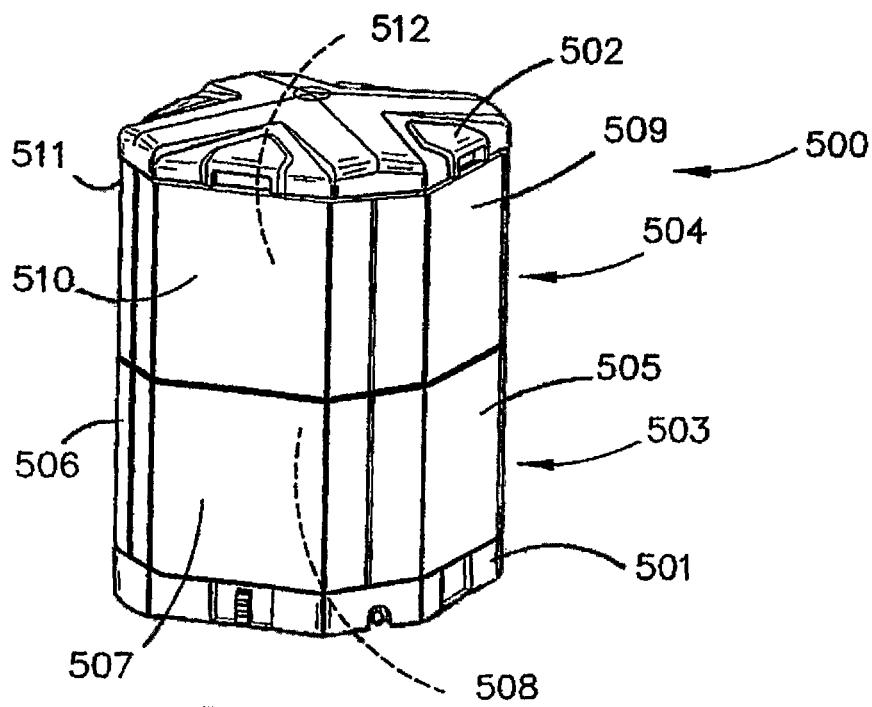
FIG. 13 is a perspective view of a still further embodiment of the invention.

FIGS. 13 to 40 show a still further embodiments of the invention. With reference to FIG. 13 a perspective view of a composting apparatus 500 is shown. The apparatus 500 has a base 501, a lid 502 and two wall segments 503 and 504. The segment 503 is formed from a first three sided wall section 505, a second three sided wall section 506, a flat wall section 507 which has an integral plug (as will be described with more detail hereinafter) and a fourth flat wall section 508 (also having a plug) opposite the wall section 507. Thus, the segment 503, is made up of the four wall sections 505, 506, 507 and 508.

The segment 504 is formed from a flat wall section 509, a three sided wall section 510, a further flat wall section 511 and a further flat three sided wall section 512 opposite the wall section 510. Thus, the wall segment 504 is made up from four wall sections 509, 510, 511 and 512.

As will be apparent from the above mentioned description the wall segment 503 and the wall segment 504 are formed from three sided panels and flat panels which are arranged so that the three sided panels of the segment 503 are staggered with respect to the three sided panels of the segment 504. A three sided wall section 505 of the segment 503 is below a flat wall section 509 of the segment 504. Thus, the segments 503 and 504 are effectively rotated 90° with respect to one another.

Figure 14:
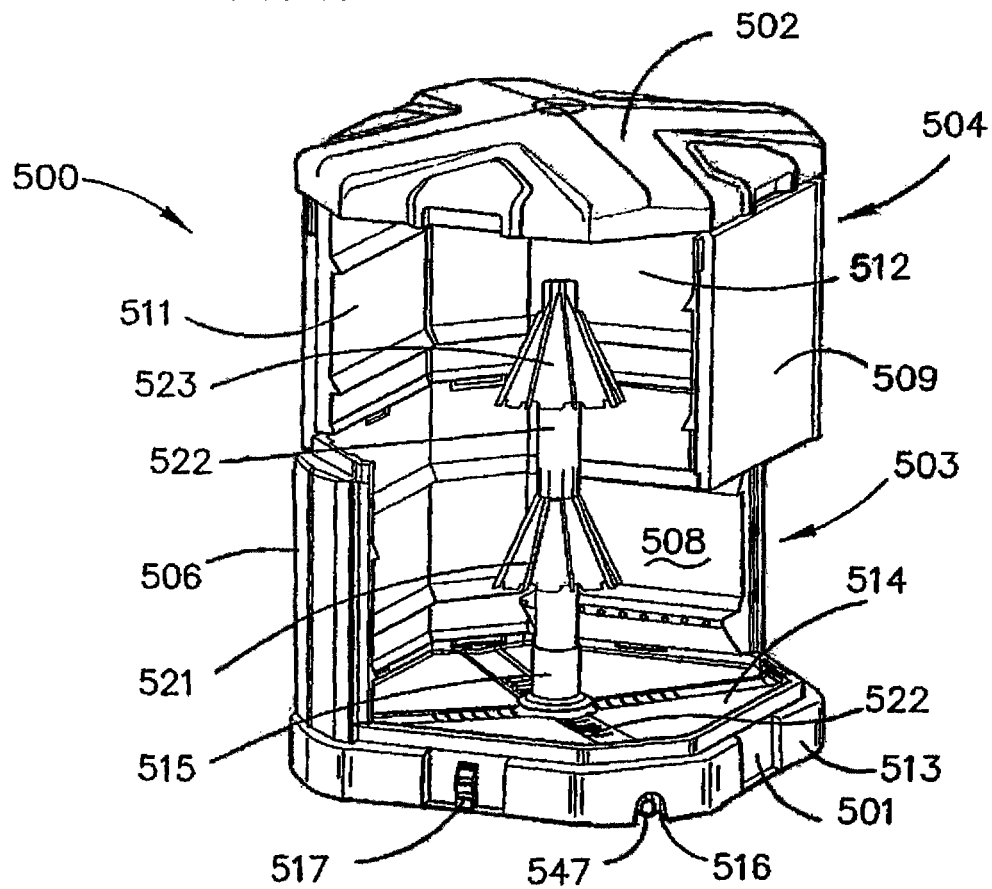
FIG. 14 is a partly exploded view of the embodiment of FIG. 13.

FIG. 14 is an exploded view showing the apparatus 500 with the wall sections 505 and 507 omitted from the wall segment 503 and the wall section 510 omitted from the segment 504.

With reference to FIG. 14 the base 501 has a peripheral side wall 513 and an upper base wall 514. A stem 515 passes through the base wall 514. The wall 513 has a cut-out 516 and an inlet 517.

An aerator pipe 520 locates into the stem 515 and supports an aerator 521 which is of generally conical configuration as will be described in more detail hereinafter. A second aerator pipe 522 locates on the aerator 521 and supports a further aerator 523 which is identical to the aerator 521.

Figure 15:
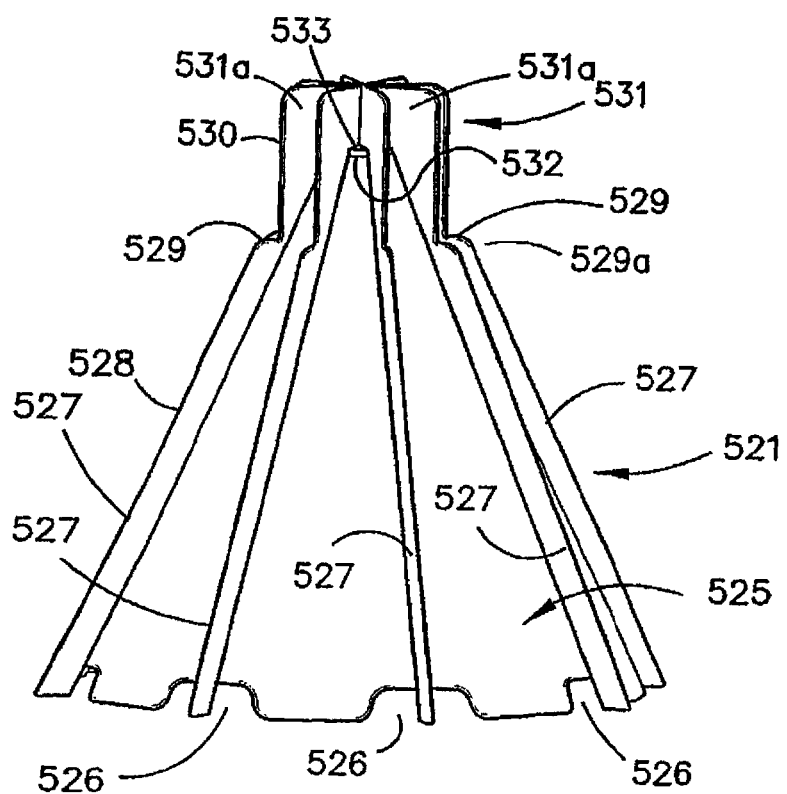
FIG. 15 is a view of an aerator use in the embodiment of FIG. 13.

As shown in FIG. 15 the aerator 521 has a generally conical peripheral wall 525 into which cut-outs 526 are formed at the lower periphery. The wall 525 is provided with a plurality of vanes 527 which have an outer edge 528 which is substantially parallel with the conical wall 525 up to an upper portion 529a of the aerator 521. At the upper portion 529a the vanes 527 transition into flutes 531a which have outer edges 530 which extends substantially vertical (that is are no longer parallel with the conical surface 525) and define a generally cylindrical stud 531. The stud 531 extends above top 532 of the conical surface 525 and the top 532 is sealed shut by a generally flat upper wall 533.

Figure 16:
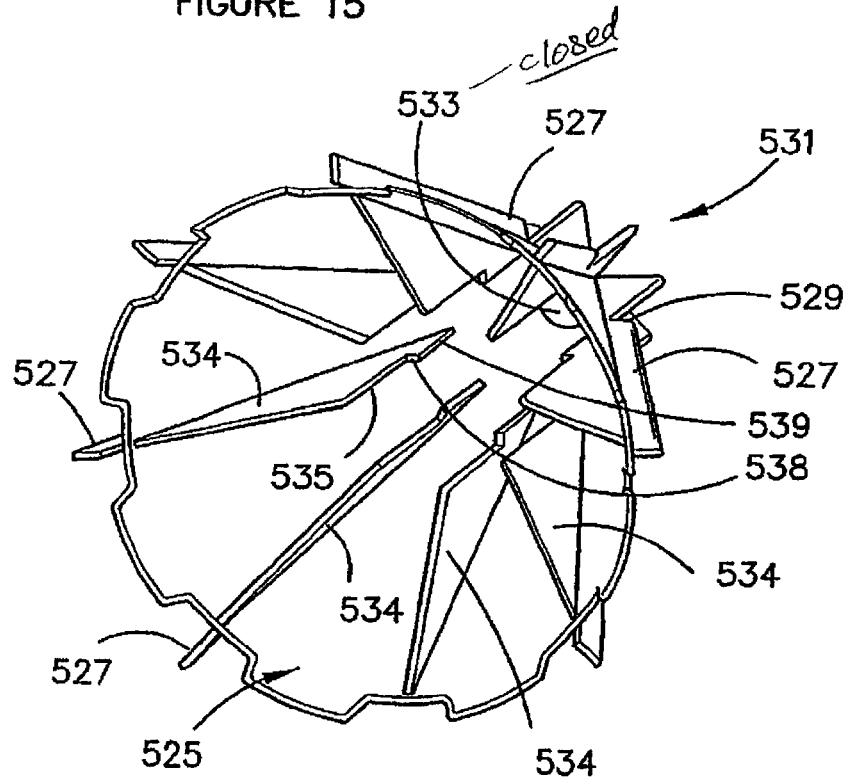
FIG. 16 is an underneath perspective view of the aerator of FIG. 15.
Figure 17:
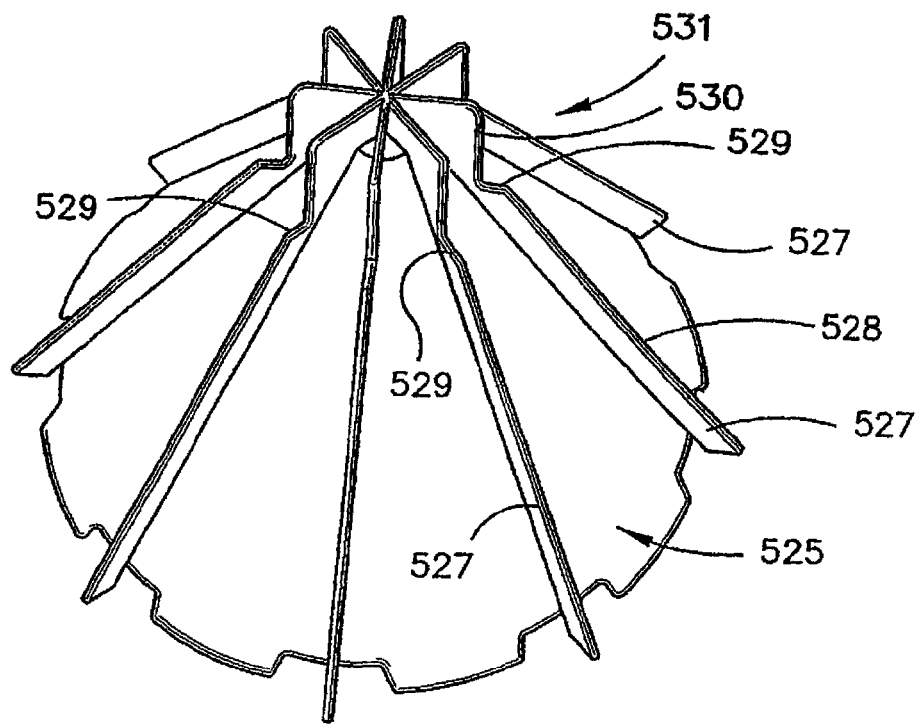
FIG. 17 is a top perspective view of the aerator of FIG. 15.

As is best shown in FIG. 16 the internal surface of the wall 525 is also provided with vanes 534 which locate in registry with a respective vein 527.

A shoulder 529 is formed where the edge 528 transitions to the edge 530. As seen in FIG. 15 the shoulder 529 is generally horizontal.

As best seen in FIG. 16 the vanes 534 have a generally vertical edge 535 which extends to a shoulder 538. A further vertical edge 539 extends upwardly from the shoulder 538 generally parallel to the edge 535. The shoulders 538 define a support for supporting the aerator 521 on aerator pipe 520.

Figure 18:
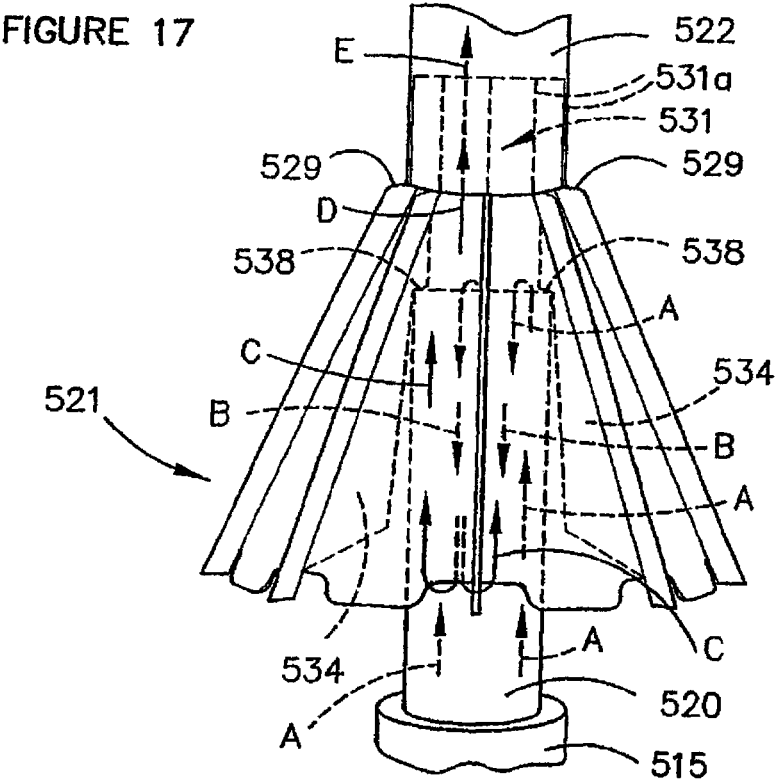
FIG. 18 is a view of the aerator in position.

The second aerator pipe 522 fits over the stud 531 as shown in FIG. 18 and rests on the shoulders 529 formed between the edges 528 and 530 of the vanes 527.

Figure 19:
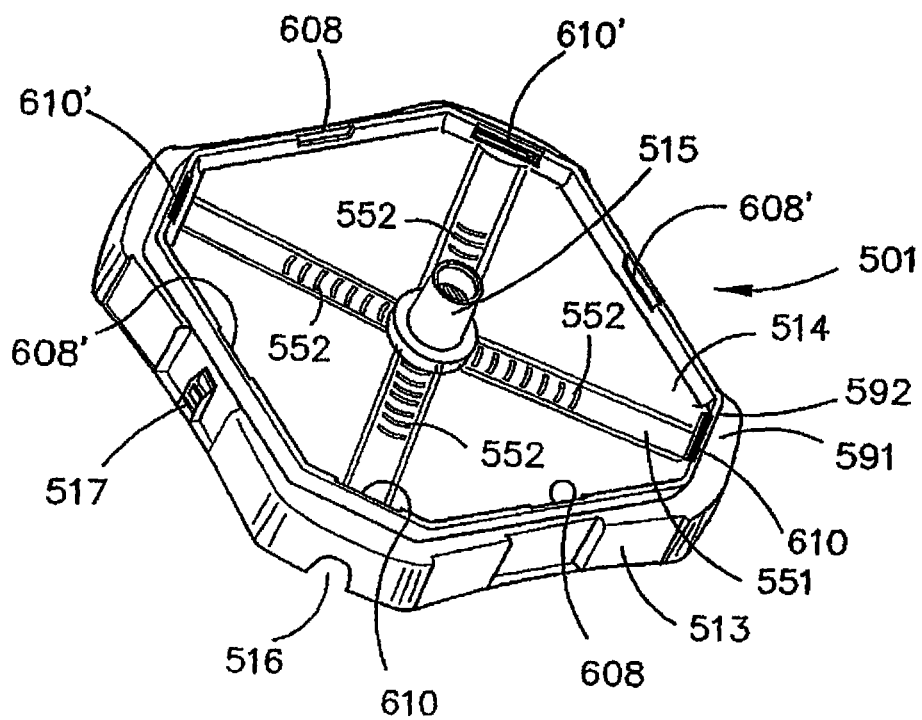
FIG. 19 is a view of a base in the embodiment of FIG. 13.
Figure 20:
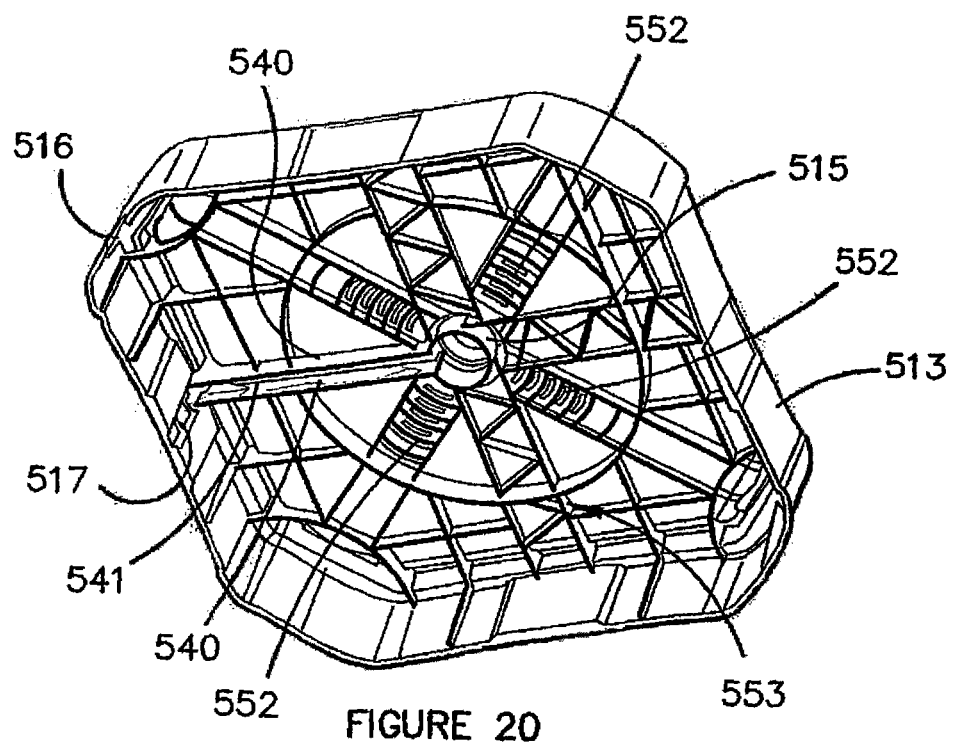
FIG. 20 is a underneath perspective view of the base of FIG. 19.

With reference to FIGS. 19 and 20 which show the base 501, the lower side of the base wall 514 shown in FIG. 20 is provided with a pair of ribs 540 which define a central channel 541 extending from inlet 517 to stem 515.

Figure 21:
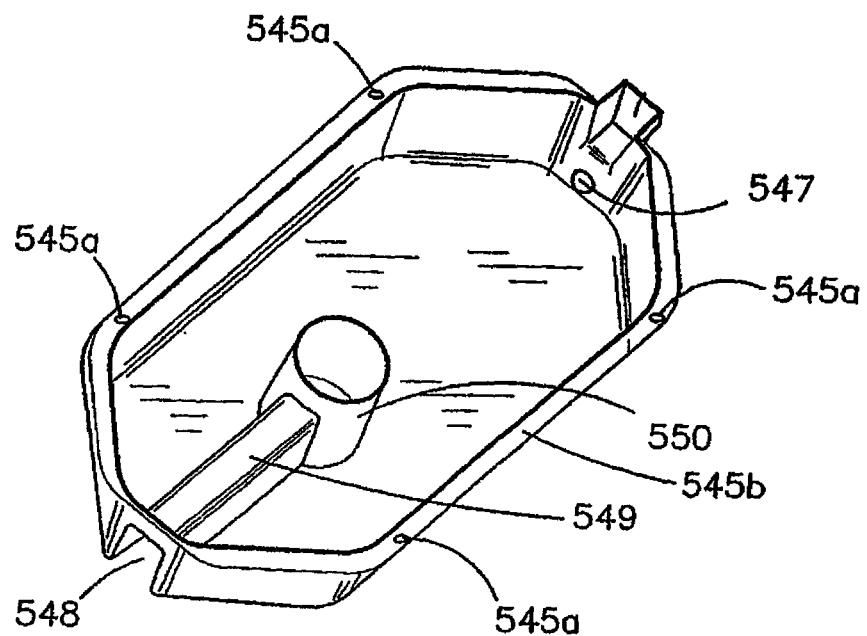
FIG. 21 is a perspective view of a leachate chamber from above.
Figure 22:
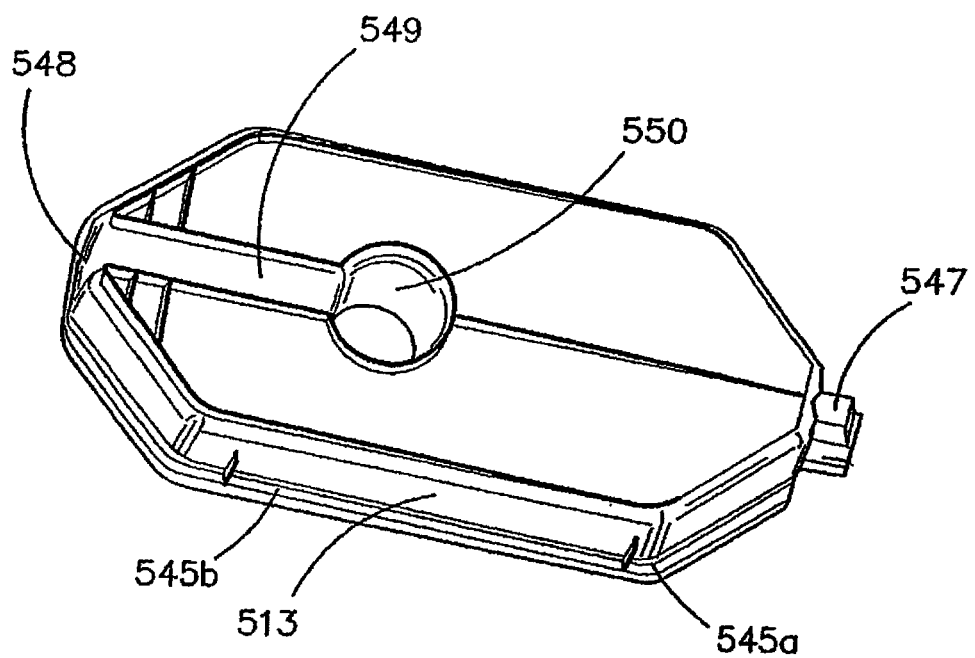
FIG. 22 is a perspective view of the leachate chamber of FIG. 21 from below.

Leachate chamber 545 which is shown in FIGS. 21 and 22 is an elongate hexangle shape and formed with an outlet 547 and an inlet 548. A passage 549 is provided between the inlet 548 and a generally cylindrical opening 550.

Figure 23:
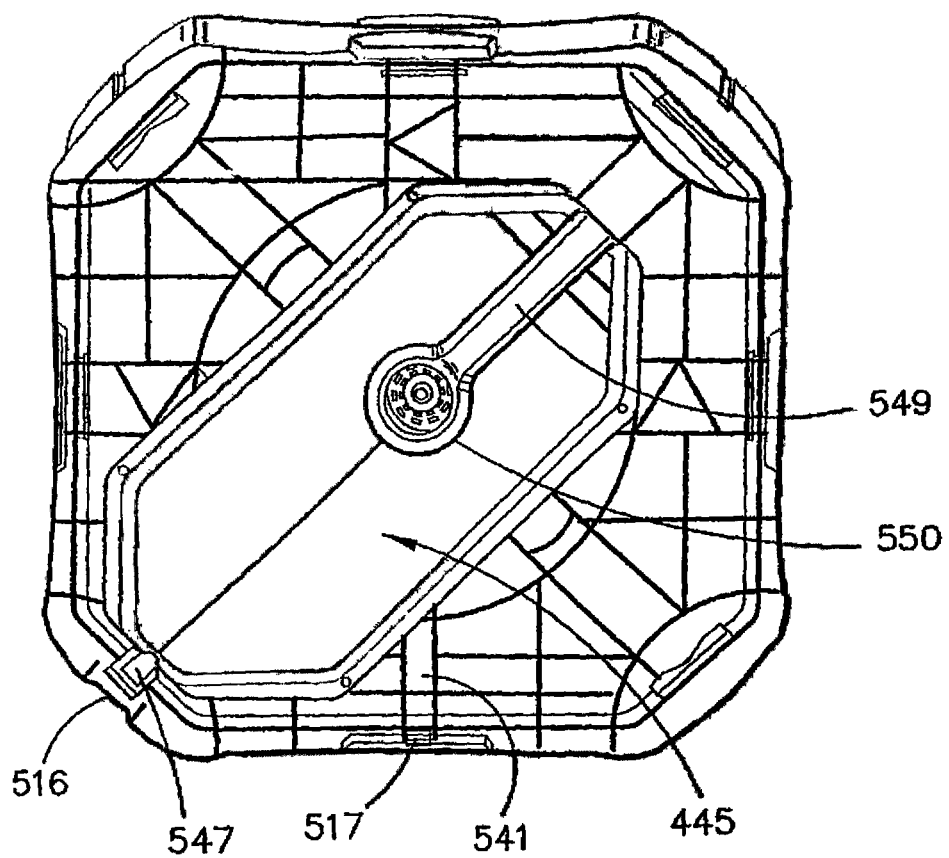
FIG. 23 is a bottom view of the composting apparatus of FIG. 13.
Figure 26:
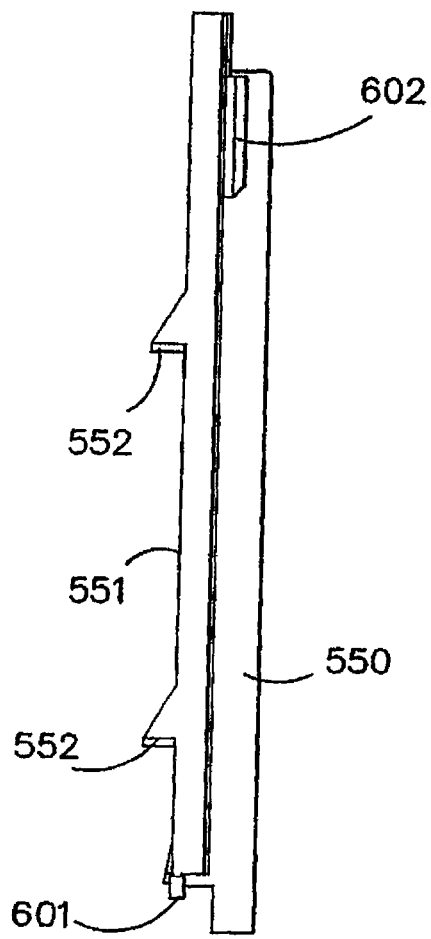
FIG. 26 is a side view of the wall section of FIGS. 24 and 25.
Figure 27:
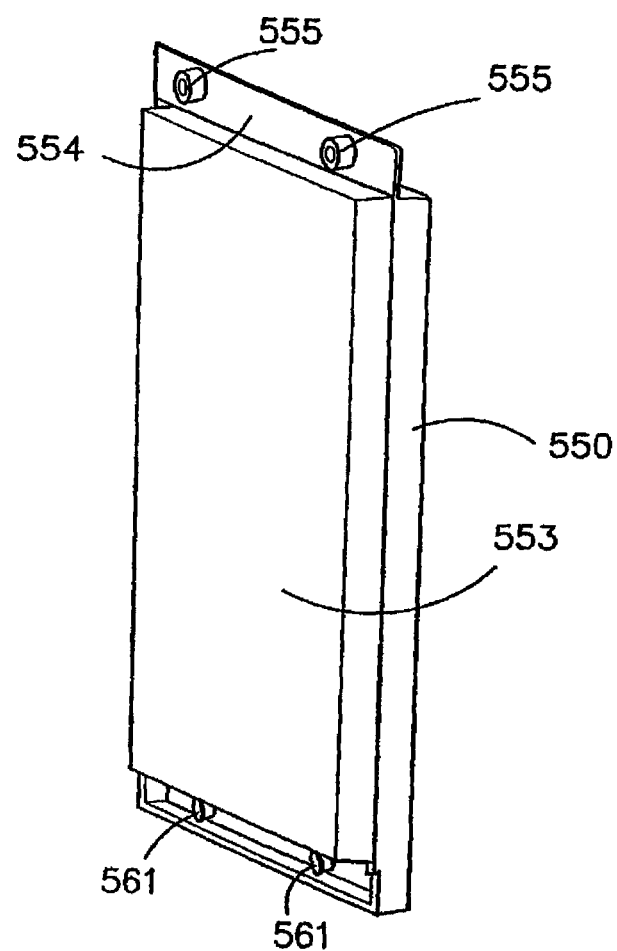
FIG. 27 is a perspective view of part of the side wall section of FIG. 26.

As shown in FIG. 23 the leachate chamber is located onto the base 501 so that the opening 550 locate over the part of the stem 515 below the wall 514. The outlet 547 locates in the cut-out 516 in the peripheral wall 513 of the base 501.

The leachate chamber 545 clips on to the base by clips (not shown) which locate in holes 545a on rim 545b so that the wall 514 forms the top of the leachate chamber 545.

The base is provided with raised reinforced sections 551 which have slots 552 which define a liquid inlet into the leachate chamber 545. The base also has reinforcing ribs 553 on its underside to provide structural integrity.

Thus, when composting material is decomposing within the apparatus 500 moisture is able to drain through the openings 552 into the leachate chamber 545 and then be drained off through outlet 547. The outlet 547 may be fitted with a tap and hose connector (not shown) for connection to a hose (not shown) if desired.

At the same time air is able to enter the inlet 517 and pass between the ribs 540 to stem 515 then up through the stem 515 and aerator pipe 520 into aerator 521. Air can also pass from beneath base 501 through passage 549 to opening 550 then to stem 515 and pipe 520. The air flows out of the aerator pipe 520 into aerator 521 and then downwardly between the vanes 534. The vanes 534 directing the air downwardly to the bottom periphery of the aerator 521 and in particular to the cut-outs 526 where the air is then able to flow out of the aerator 521 and up through the composting mass.

The vanes 527 facilitate the upward flow and also act as anti-compaction devices to prevent compaction of composting material about the aerator 521 which would prevent the upward flow of air. Thus, the vanes 527 ensure that the composting material does not compact down onto the surface 525 so that air is able to flow up along side the surface 525 between the vanes 527 and also migrate out into the composting material surrounding the aerator 521.

Some of the air which passes up along the surface 525 between the vanes 527 is able to enter the pipe 522 through the bottom of the pipe 522 and between the flutes 531a as shown by the arrows in FIG. 18. That is, because the pipe 522 sits on the shoulder 529 the bottom pipe is open to the space between the vanes 527 so air can flow up through that opening between the flutes 531a.

Thus, as shown in FIG. 18, air flows up pipe 520 as shown by arrows A, over the top of the pipe 520, into interior chamber 680 delivered by the wall 525 and down the internal surface of the aerator 521 as shown by arrows B, then up the outer surface of the aerator 521 between the vanes 527 as shown by arrows C (where some of the air is able to migrate out into the composting mass), then into pipe 522 at shoulder 529, between the flutes 531a as shown by arrow D, and up through pipe 522 as shown by arrow E to aerator 523. Once again the vanes 527 on the aerator 523 act to prevent compaction of material around the aerator 523 which would otherwise prevent airflow out from the aerator 523 into the composting mass.

Figure 28:
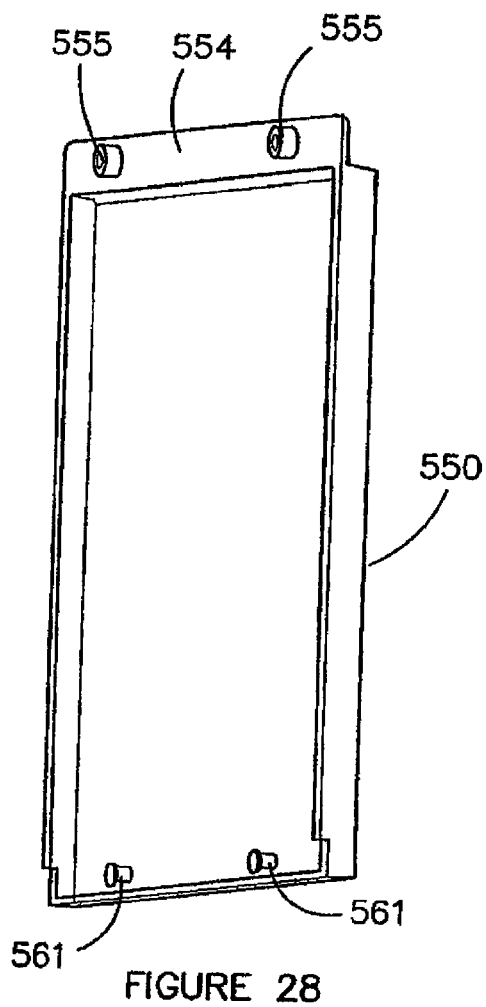
FIG. 28 is a perspective view of part of the section of FIG. 27.
Figure 29:
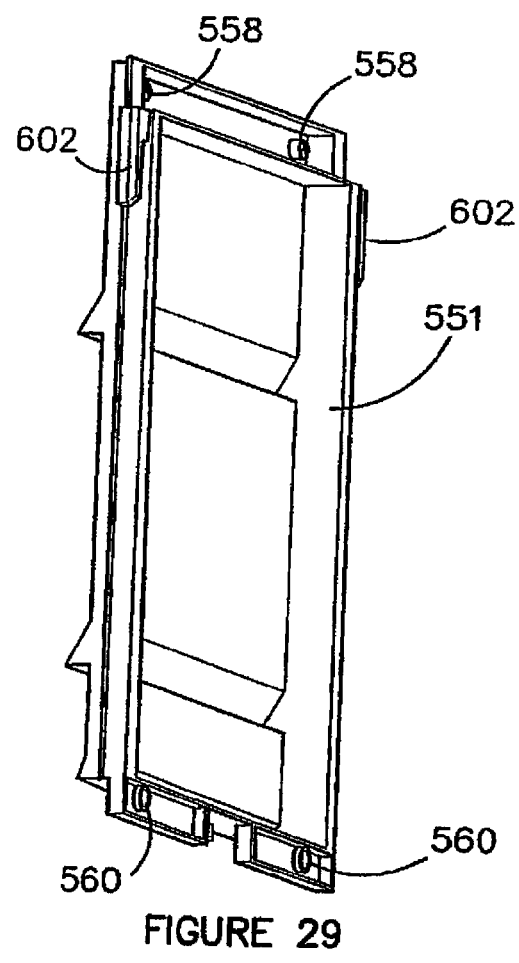
FIG. 29 is a view of part of the section of FIG. 26.

FIGS. 24 to 29 show the wall sections 509 and 511. Each wall section is of the same structure as is apparent from the above description. The wall section is provided with an outer skin 550 and an inner skin 551. As best shown in FIG. 25 the inner skin 551 is provided with inwardly projecting ribs 552. The skin 551 is of generally tray shaped design and carries an insulating block 553. The skin 551 has an upper flange 554 which has bosses 555 for receiving pins 528 on inner skin 551. The pins 558 are generally flexible so that they clip into the bosses 555 to lock the skins 551 and 550 together. As shown in FIG. 29 the skin 551 is also a generally tray shaped in configuration and includes bosses 560 for receiving pins 561 on the skin 551. FIG. 28 shows a view of the skin 550 without the insulating pad 553.

The projecting ribs 552 prevent air flow directly up the internal surface of the wall sections in a space which may result as the composting material shrinks within the apparatus 500. The provision of the ribs 552 tends to direct air flow away from the inner surface of the wall sections and around the inner periphery of the wall sections and into the composting material.

As is shown in the drawings the ribs 552 extend all the way about the periphery of the wall sections on the internal surface of the composting apparatus so as to form continuous ribs to prevent air flow up the side of the wall sections and distribute the air flow as discussed previously.

Figure 30:
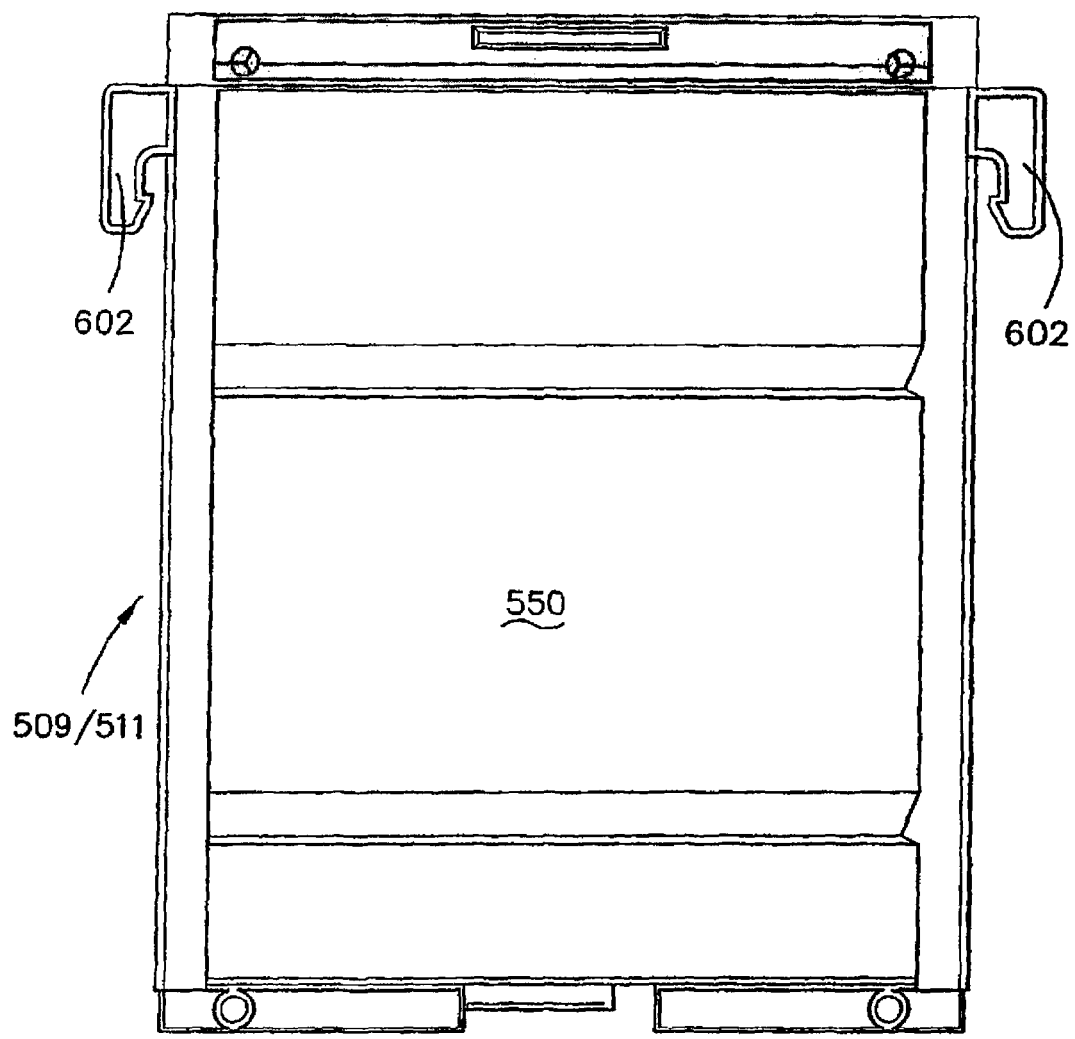
FIG. 30 is a front view of the part of the wall section of FIG. 29.

The flat wall sections 509 and 511 are provided with L-shaped lugs 602 at their upper portions as is best shown in FIGS. 24, 25, 26, 29 and in the enlarged view forming FIG. 30.

Figure 31:
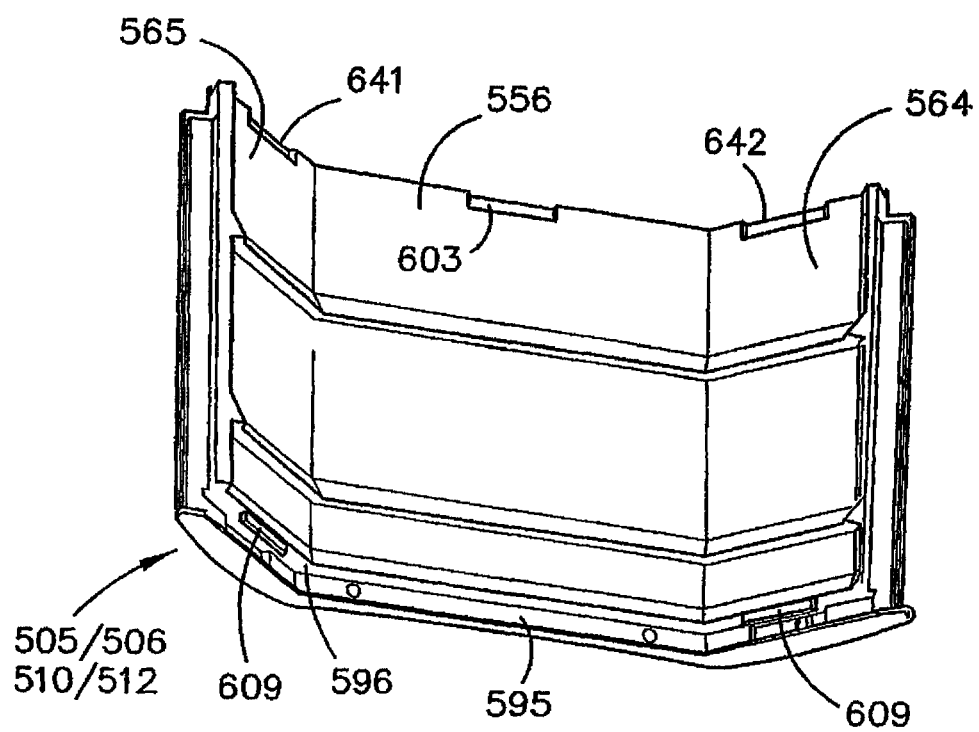
FIG. 31 is a view of a further wall section.
Figure 32:
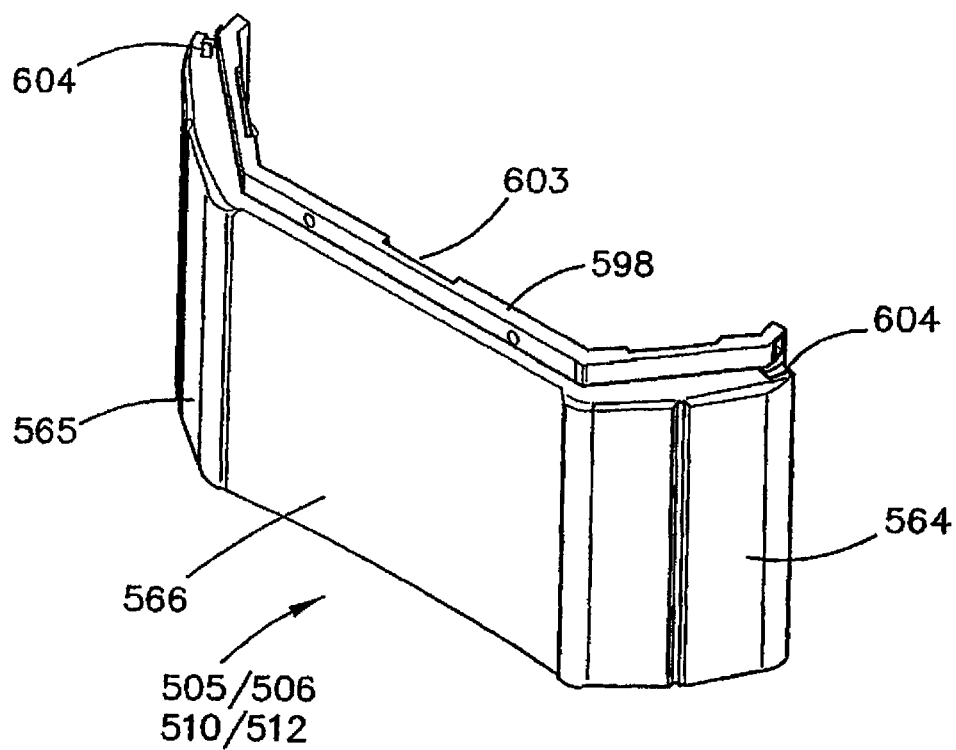
FIG. 32 is a perspective view from the outside of the wall section of FIG. 31.

FIGS. 31 and 32 show the wall sections 505, 506, 510 and 512. These wall sections are three sided wall sections having small wall portions 564 and 565 joined by a central larger wall portion 566. The wall sections shown in FIGS. 30 and 31 are formed from an inner skin, outer skin and insulating block in the same manner as the wall sections 509 and 511. The skins connect together in the same manner as described with reference to FIGS. 24 to 29.

The wall sections 505, 506, 510 and 512 have an upper horizontal ledge 597 and an upstanding wall flange 598 inwardly of the ledge 597. The ledge 597 is provided with aperture 604 at their ends for receiving lugs 602 of the wall sections 509 and 511 as will be described hereinafter.

Figure 33:
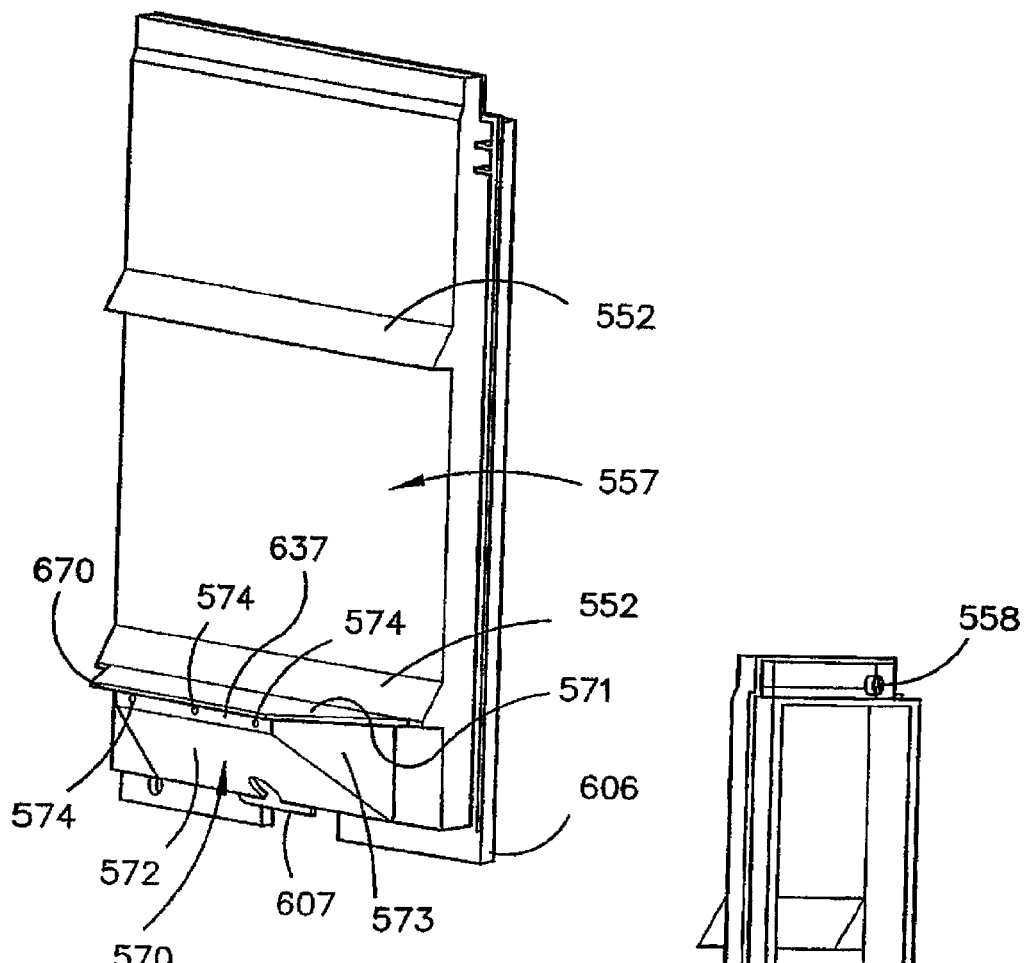
FIG. 33 is a view of a still further wall section including a plug.

The wall sections 507 and 508 have an integral plug 570 which projects inwardly into the composting container 500. The plug 570 is generally triangular in shape as shown in FIG. 33 and has an upper horizontal wall 571 and a lower inclined wall 572 together with vertical side walls 573 and front wall 537. The top wall 571 has an eave 670 and front wall 637. Outlet openings 574 are provided in wall 637. The plug 572 acts in the same way as the plug described with reference to FIGS. 11 and 12.

Figure 34:
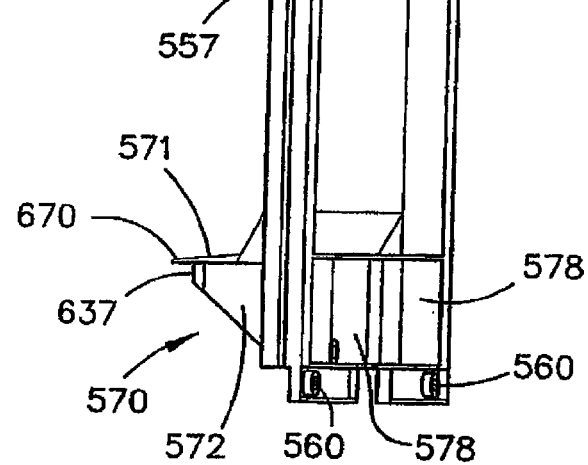
FIG. 34 is a perspective view of part of the wall section of FIG. 33 from the outside.

FIG. 34 is a view of inner skin 577 where it can be seen that the plug 570 is provided with internal baffles 578. FIG. 34 is a view of the outer skin 579 and insulating block 580. The skins 577 and 579 join together in the same manner as described with reference to FIGS. 24 to 29 and like reference numbers indicate like parts of those previously described.

Figure 35:
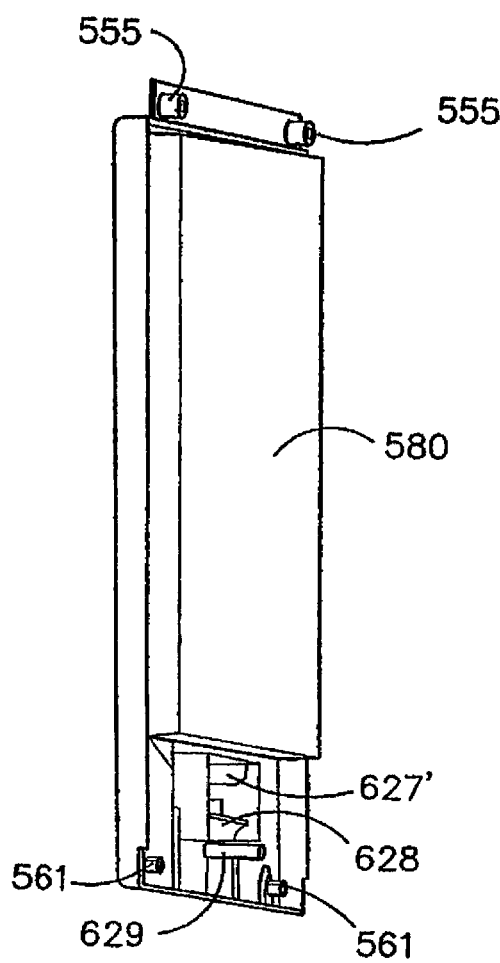
FIG. 35 is a perspective view of still a further part of the wall section used with the part shown in FIGS. 33 and 34.
Figure 36:
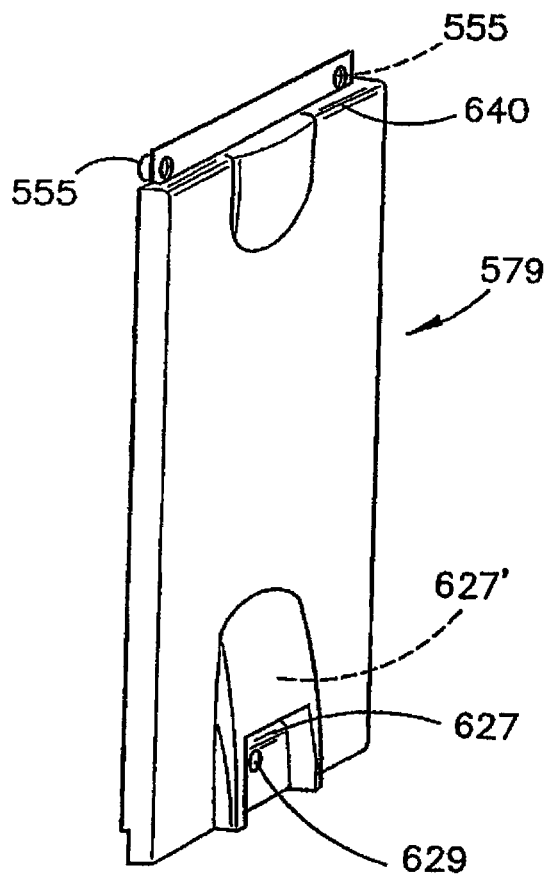
FIG. 36 is a view of part of the section shown in FIG. 35.

FIG. 35 is a view from the outside of the skin 579. The skin 579 has a hand grip 627 which facilitates handling of the wall section and its location in place. The hand grip 627 also allows the wall section 507 to be removed so that compost can be emptied from the apparatus. Hand grip 627 also provides an air passage 627' to the plug 570. As shown in FIG. 35 the air passage 627' is surrounded by a box section 628 in which may be located a foam or other air permeable material to prevent insects and the like from passing through the opening 627' into the interior of the compost apparatus 500. An air outlet tube 629 is provided (as shown in FIG. 34) for venting heavy gases which may be generated during composting of material, from the composting apparatus.

As best shown in FIG. 14 and FIG. 19 the base 501 is provided with a peripheral generally horizontal ledge 591 and an upstanding flange 592. The wall segment 503 is assembled on the base 501 by locating the wall section 505 shown in FIG. 30 so that outer flange 595 of the wall section 505 sits on peripheral ledge 591 and a shoulder 596 sits on the top of inner wall section 592. The wall section 505 is provided with a pair of lugs 609 which locate into cut-outs 610 (see FIG. 19) of base 501. The wall section 506 is the same as the wall section 505 and locates in the same manner but with the lugs 609 locating in cut-outs 610'. The wall sections 507 and 508 locate on base 501 in the same manner but with lugs 607 locating in respective cut-outs 608'. The cut-outs 608 shown in FIG. 19 are not used in the configuration described above. However, if the wall segments are rotated 90° then those cut-outs would be used instead of the cut-out 608'.

As best shown in FIG. 25 wall sections 509 and 511 have a lower shoulder 599 and a downwardly projecting flange 600. The shoulder 599 sits on flange 598 and flange 600 sits on outer horizontal ledge 597 of the respective lower wall section 505 and 506. As shown in FIG. 25 the inner skin 550 is provided with a lug 601. The lug 601 locates in cut-out portion 603 of the wall section 505 shown in FIG. 31.

Similarly the wall sections 509 and 511 sit on a wall segment 503 by a flange 595 sitting on horizontal ledge 640 of a respective wall section 507 and 508 and also on horizontal ledge 597 of respective wall section 505 or 506. The respective lugs 609 of the wall sections 510 and 512 locate in cut-outs 641 and 642 of the wall sections 505 and 506.

Thus, the wall sections are located with the respective lugs located in respective cut-outs by positioning the respective lugs above the cut-outs and sliding the wall sections downwardly. Similarly the wall sections can be removed by sliding the wall sections upwardly until the lugs disengage from the cut-outs and then pulling the wall sections away from the composting apparatus.

Figure 37:
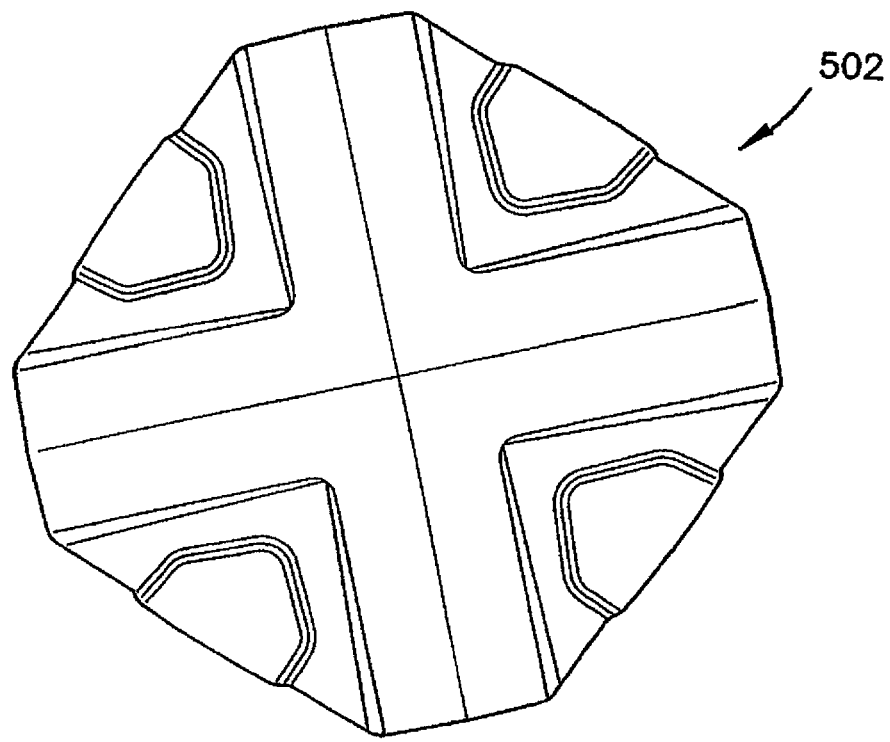
FIG. 37 is a plan view of the lid.
Figure 38:
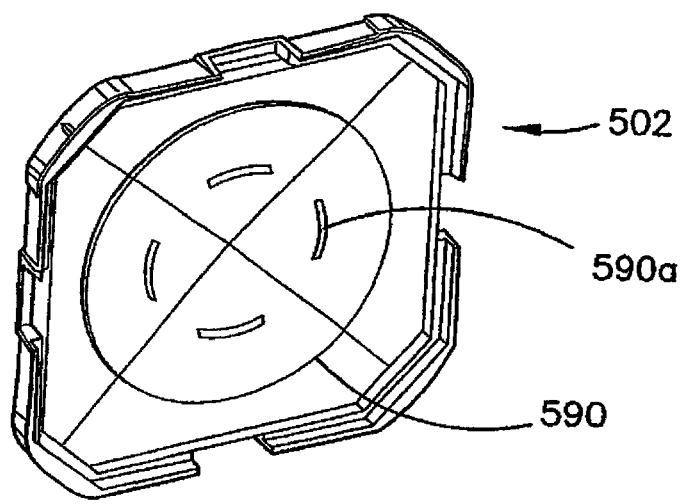
FIG. 38 is a view of the lid of FIG. 35 from underneath.

FIGS. 37 and 38 show the lid 502. The lid 502 has a circular ridge 590 and a part circular inner ridge 590a which facilitates dripping of condensation formed on the underside of the lid 502 back into the composting mass. The lid 502 can be a one piece structure or can be formed of two stems with an insulating block between the two stems.

The lid 502 is provided with wall portions and lugs which fit into the corresponding wall portions and cut-outs in the wall sections 509, 510, 511 and 512.

Figure 39:
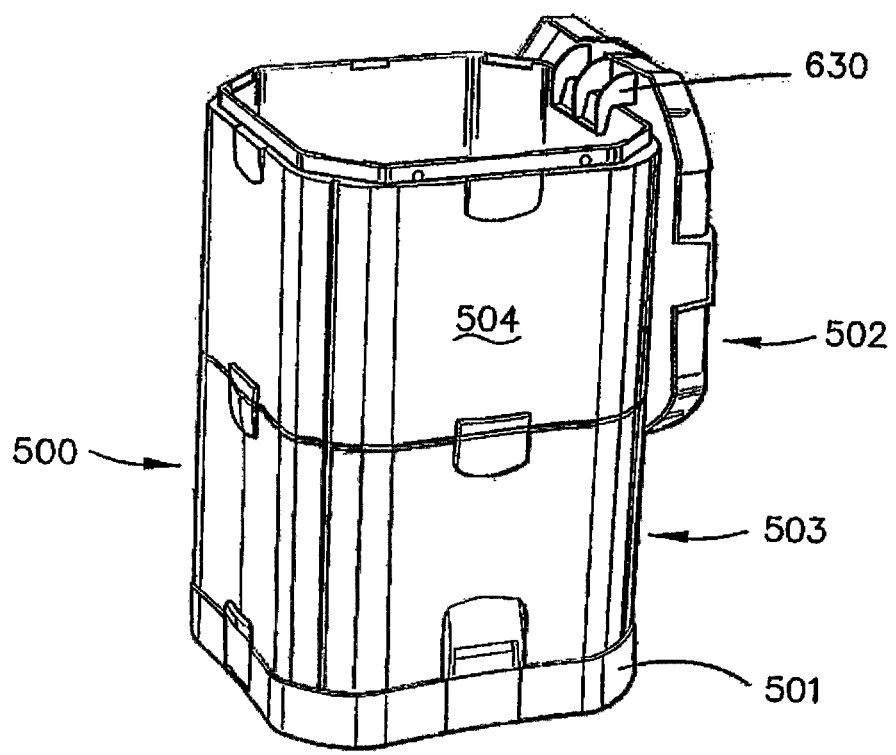
FIGS. 39 and 40 show a lid according to a second embodiment.
Figure 40:
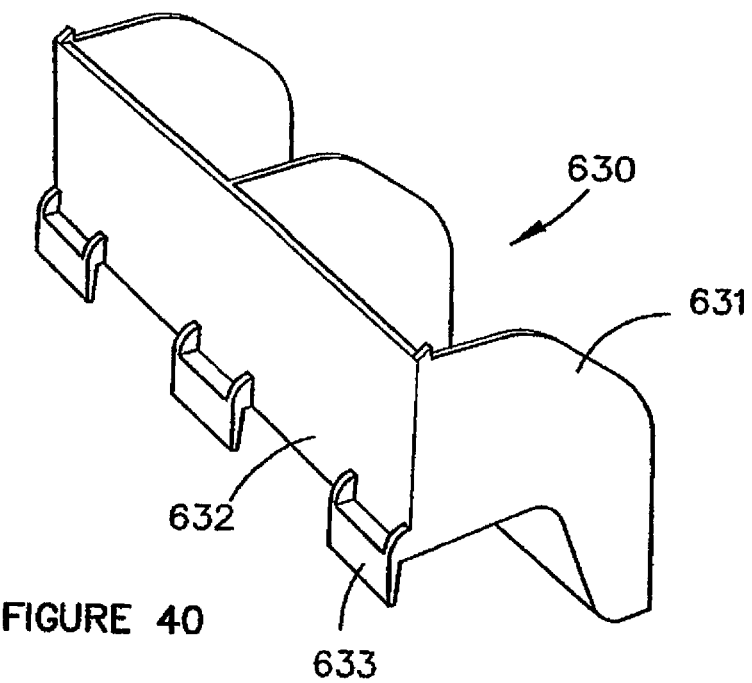

In a further embodiment as shown in FIG. 39 the lid 502 may be provided with a bracket 630 so that it can be hung from the peripheral side wall of the composting apparatus 500. The bracket 630 is shown in FIG. 40 and comprises three lugs 631 connected to a rear wall 632. Clips 633 are attached to the rear wall 632 and locate in slots (not shown) in the underside of the lid 502 to secure the bracket in place. The bracket 630 is positioned so that it does not interfere with location of rib 502 on the apparatus 500.

In order to extend the size of the composting apparatus additional wall sections 504 and aerators 523 can be added. This is done simply by adding another wall segment 504 the same as that shown in FIG. 14 on top of the wall segment 504. An additional aerator pipe 522 is located on the aerator 523 and a further aerator is located on the additional pipe. Thus, the apparatus can be increased in size to three segments and three aerators. The aerators will operate in the same manner as the two aerators previously described. Still further segments can be added if desired. Further still, a single segment bin can be provided by doing away with the second pipe 522 and aerator 523 and the upper wall segment 504 so that the lid 502 is located on the lower segment 503.

Since modifications within the spirit and scope of the invention may readily be effected by persons skilled within the art, it is to be understood that this invention is not limited to the particular embodiment described by way of example hereinabove.

In the claims which follow and in the preceding description of the invention, except where the context requires otherwise due to express language or necessary implication, the word "comprise", or variations such as "comprises" or "comprising", is used in an inclusive sense, i.e. to specify the presence of the stated features but not to preclude the presence or addition of further features in various embodiments of the invention.

The invention claimed is:

1. A composting apparatus, comprising:
a container for receiving material to be composted;
an aerator located in the container, the aerator comprising an aerator pipe with a cap and having at least one opening for allowing air to pass from the aerator into an interior of the container for facilitating aerobic decomposition of material to form compost;
an airflow path that supplies air from outside the container to the aerator that is in communication with the aerator pipe;
a base in the container for supporting material to be composted and having an upper base wall with an opening through which the aerator pipe is supported to extend into the interior of the container;
a leachate chamber on the underside of the upper base wall to receive leachate formed by the composting material;
wherein the upper base wall has multiple openings for allowing leachate to flow from the composting material into the leachate chamber; and
an outlet from the leachate chamber for drainage of the leachate from the chamber to the outside of the container.

2. A composting apparatus as claimed in claim 1, wherein the upper base wall forms the top of the leachate chamber, wherein the multiple openings are slots to allow leachate to flow from the composting material into the leachate chamber.

3. A composting apparatus as claimed in claim 1, wherein the outlet communicates with a lower part of the leachate chamber.

4. A composting apparatus as claimed in claim 3, wherein the lower wall of the base is shaped to facilitate flow of leachate within the chamber to the outlet.

5. A composting apparatus as claimed in claim 1, wherein the base provides an airflow passage forming part of the airflow path for supplying air from outside the container to the aerator.

6. A composting apparatus as claimed in claim 5, wherein the airflow passage extends upwardly through the leachate chamber.

7. A composting apparatus as claimed in claim 1, wherein the leachate chamber is defined between the upper base wall and a lower wall of the base, and the lower wall is provided with an air inlet passage for flow of air from outside the container to the aerator pipe connected to the aerator.

8. A composting apparatus as claimed in claim 1, wherein the container is formed from a plurality of separate segments, each segment including an outer peripheral wall, and wherein the segments are located one above another in order to form the composting container and the size of the composting container can be increased by adding additional segments to an uppermost one of the segments.

9. A composting apparatus as claimed in claim 1, wherein the aerator can be extended by locating a further aerator on the first said aerator so that air is supplied to new material added to the container to facilitate the aerobic decomposition of that material.

10. A composting apparatus of claim 8, wherein each segment comprises adjacent wall sections, and each wall section is formed from an outer skin, an inner skin and an insulating block located between the inner skin and the outer skin.

11. A composting apparatus of claim 10, wherein the inner skin is provided with inwardly projecting ribs extending all the way about a periphery of the wall section.

12. A composting apparatus of claim 1, comprising a lid, wherein the lid includes a circular ridge and/or a part circular ridge on an underside of the lid.

* * * * *